US010285941B2

(12) United States Patent
Kotyla

(10) Patent No.: US 10,285,941 B2
(45) Date of Patent: *May 14, 2019

(54) AMPHIPHILIC ENTITY NANOPARTICLES

(71) Applicant: Anterios, Inc., New York, NY (US)

(72) Inventor: Timothy Kotyla, Natick, MA (US)

(73) Assignee: Anterios, Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/636,927

(22) Filed: Jun. 29, 2017

(65) Prior Publication Data

US 2017/0360704 A1 Dec. 21, 2017

Related U.S. Application Data

(63) Continuation of application No. 14/182,919, filed on Feb. 18, 2014, now Pat. No. 9,724,299, which is a continuation of application No. 12/517,154, filed as application No. PCT/US2007/086018 on Nov. 30, 2007, now abandoned.

(60) Provisional application No. 60/872,198, filed on Dec. 1, 2006.

(51) Int. Cl.
| | |
|---|---|
| *A61K 8/11* | (2006.01) |
| *A61K 9/107* | (2006.01) |
| *A61K 8/67* | (2006.01) |
| *A61K 8/73* | (2006.01) |
| *A61K 8/85* | (2006.01) |
| *A61K 8/99* | (2017.01) |
| *A61K 9/00* | (2006.01) |
| *A61K 9/51* | (2006.01) |
| *A61Q 19/08* | (2006.01) |
| *B82Y 5/00* | (2011.01) |
| *A61K 8/02* | (2006.01) |

(52) U.S. Cl.
CPC .......... *A61K 9/1075* (2013.01); *A61K 8/0291* (2013.01); *A61K 8/11* (2013.01); *A61K 8/678* (2013.01); *A61K 8/73* (2013.01); *A61K 8/85* (2013.01); *A61K 8/99* (2013.01); *A61K 9/0014* (2013.01); *A61K 9/5153* (2013.01); *A61Q 19/08* (2013.01); *B82Y 5/00* (2013.01); *A61K 2800/413* (2013.01); *Y02A 50/469* (2018.01); *Y10T 428/2982* (2015.01)

(58) Field of Classification Search
CPC .. A61K 2800/413; A61K 8/0291; A61K 8/11; A61K 8/678; A61K 8/73; A61K 8/85; A61K 8/99; A61K 9/0014; A61K 9/1075; A61K 9/5153; A61Q 19/08; B82Y 5/00; Y10T 428/2982
See application file for complete search history.

(56) References Cited

U.S. PATENT DOCUMENTS

| | | | |
|---|---|---|---|
| 3,725,540 | A | 4/1973 | Wahl |
| 4,172,149 | A | 10/1979 | Pinto et al. |
| 4,533,254 | A | 8/1985 | Cook et al. |
| 4,908,154 | A | 3/1990 | Cook et al. |
| 5,008,110 | A | 4/1991 | Benecke et al. |
| 5,152,923 | A | 10/1992 | Weder et al. |
| 5,374,614 | A | 12/1994 | Behan et al. |
| 5,401,243 | A | 3/1995 | Borodic |
| 5,470,577 | A | 11/1995 | Gilchrest et al. |
| 5,502,045 | A | 3/1996 | Miettinen et al. |
| 5,510,118 | A | 4/1996 | Bosch et al. |
| 5,576,016 | A | 11/1996 | Amselem et al. |
| 5,591,767 | A | 1/1997 | Mohr et al. |
| 5,629,021 | A | 5/1997 | Wright |
| 5,651,991 | A | 7/1997 | Sugiyama et al. |
| 5,652,274 | A | 7/1997 | Martin |
| 5,660,858 | A | 8/1997 | Parikh et al. |
| 5,670,484 | A | 9/1997 | Binder |
| 5,672,358 | A | 9/1997 | Tabibi et al. |
| 5,683,712 | A | 11/1997 | Cavazza |
| 5,753,241 | A | 5/1998 | Ribier et al. |
| 5,766,605 | A | 6/1998 | Sanders et al. |
| 5,851,452 | A | 12/1998 | Vallet Mas et al. |
| 5,858,410 | A | 1/1999 | Muller et al. |
| 5,925,341 | A | 7/1999 | Cervantes et al. |
| 5,932,562 | A | 8/1999 | Ostlund, Jr. |
| 5,948,433 | A | 9/1999 | Burton et al. |
| 5,965,154 | A | 10/1999 | Haralambopoulos |

(Continued)

FOREIGN PATENT DOCUMENTS

| | | |
|---|---|---|
| CA | 2067754 A1 | 2/1992 |
| CA | 2465123 A1 | 5/2003 |

(Continued)

OTHER PUBLICATIONS

Aoki K.R., Botulinum neurotoxin serotype A and B preparations have different safety margins in preclinical models of muscle weakening efficacy and systemic safety, Toxicon 40:923-928 (2002).

(Continued)

*Primary Examiner* — Ernst V Arnold

(74) *Attorney, Agent, or Firm* — McCarter & English, LLP; Marcie B. Clarke; Joshua J. Galgano

(57) ABSTRACT

The present invention provides nanoparticle compositions comprising AE nanoparticles. The present invention provides AE nanoparticles comprising one or more amphiphilic entities and pharmaceutical compositions comprising AE nanoparticles. The present invention provides methods of manufacturing AE nanoparticles. The present invention provides methods of delivering a biologically active agent to a subject by administering AE nanoparticles containing a biologically active agent to a subject.

20 Claims, No Drawings

(56) References Cited

U.S. PATENT DOCUMENTS

| | | |
|---|---|---|
| 5,994,414 A | 11/1999 | Franco et al. |
| 6,007,856 A | 12/1999 | Cox et al. |
| 6,010,715 A | 1/2000 | Wick et al. |
| 6,039,936 A | 3/2000 | Restle et al. |
| 6,087,327 A | 7/2000 | Pearce et al. |
| 6,165,500 A | 12/2000 | Cevc |
| 6,224,853 B1 | 5/2001 | Steel et al. |
| 6,265,180 B1 | 7/2001 | Zuelli et al. |
| 6,274,150 B1 | 8/2001 | Simonnet et al. |
| 6,312,708 B1 | 11/2001 | Donovan |
| 6,358,917 B1 | 3/2002 | Carruthers et al. |
| 6,387,411 B2 | 5/2002 | Bruce et al. |
| 6,429,189 B1 | 8/2002 | Borodic |
| 6,455,058 B1 | 9/2002 | Sun et al. |
| 6,458,373 B1 | 10/2002 | Lambert et al. |
| 6,558,941 B2 | 5/2003 | Zuelli et al. |
| 6,573,241 B1 | 6/2003 | Bigalke et al. |
| 6,589,588 B1 | 7/2003 | Wester et al. |
| 6,620,419 B1 | 9/2003 | Lintner |
| 6,623,780 B1 | 9/2003 | Stevens et al. |
| 6,632,440 B1 | 10/2003 | Quinn et al. |
| 6,670,322 B2 | 12/2003 | Goodnough et al. |
| 6,688,311 B2 | 2/2004 | Hanin |
| 6,720,001 B2 | 4/2004 | Chen et al. |
| 6,765,001 B2 | 7/2004 | Gans et al. |
| 6,835,395 B1 | 12/2004 | Semple et al. |
| 6,835,895 B1 | 12/2004 | Asai et al. |
| 6,861,066 B2 | 3/2005 | Van de Casteele |
| 6,869,610 B2 | 3/2005 | Aoki et al. |
| 6,890,560 B2 | 5/2005 | Seo et al. |
| 6,902,737 B2 | 6/2005 | Quemin |
| 6,939,852 B2 | 9/2005 | Graham |
| 6,974,578 B1 | 12/2005 | Aoki et al. |
| 6,974,579 B2 | 12/2005 | Brin et al. |
| 7,001,602 B2 | 2/2006 | Schmidt |
| 7,125,858 B2 | 10/2006 | Filion et al. |
| 7,226,605 B2 | 6/2007 | Suskind et al. |
| 7,228,259 B2 | 6/2007 | Freund |
| 7,255,865 B2 | 8/2007 | Walker |
| 7,384,918 B2 | 6/2008 | Graham |
| 7,419,996 B2 | 9/2008 | Chow et al. |
| 7,507,419 B2 | 3/2009 | Coleman, III |
| 7,531,193 B2 | 5/2009 | Demarne et al. |
| 7,763,663 B2 | 7/2010 | McCarthy et al. |
| 8,318,181 B2 | 11/2012 | Edelson et al. |
| 8,658,391 B2 | 2/2014 | Edelson |
| 9,486,409 B2 | 11/2016 | Edelson et al. |
| 9,649,266 B2 | 5/2017 | Edelson |
| 9,724,299 B2 | 8/2017 | Kotyla |
| 2002/0015721 A1 | 2/2002 | Simonnet et al. |
| 2002/0048596 A1 | 4/2002 | Cevc |
| 2002/0098215 A1 | 7/2002 | Douin et al. |
| 2002/0107199 A1 | 8/2002 | Walker |
| 2002/0155084 A1 | 10/2002 | Roessler et al. |
| 2002/0165179 A1 | 11/2002 | Baker |
| 2002/0187164 A1 | 12/2002 | Borodic |
| 2003/0072801 A1 | 4/2003 | Curatolo et al. |
| 2003/0077240 A1 | 4/2003 | LeGrow et al. |
| 2003/0086888 A1 | 5/2003 | LeGrow et al. |
| 2003/0108597 A1 | 6/2003 | Chancellor et al. |
| 2003/0113349 A1 | 6/2003 | Coleman |
| 2003/0138465 A9 | 7/2003 | Douin et al. |
| 2003/0157138 A1 | 8/2003 | Eini et al. |
| 2003/0194412 A1 | 10/2003 | Baker et al. |
| 2003/0206955 A1 | 11/2003 | Sonneville-Aubrun et al. |
| 2003/0211140 A1 | 11/2003 | Mantripragada et al. |
| 2003/0224020 A1 | 12/2003 | Zabudkin et al. |
| 2003/0229141 A1 | 12/2003 | Yu et al. |
| 2004/0003324 A1 | 1/2004 | Uhlig et al. |
| 2004/0005370 A1 | 1/2004 | Breton |
| 2004/0009180 A1 | 1/2004 | Donovan |
| 2004/0009936 A1 | 1/2004 | Tang et al. |
| 2004/0028635 A1 | 2/2004 | Chauvierre et al. |
| 2004/0033202 A1 | 2/2004 | Cooper et al. |
| 2004/0033241 A1 | 2/2004 | Donovan |
| 2004/0037853 A1 | 2/2004 | Borodic |
| 2004/0048836 A1 | 3/2004 | Wilmott |
| 2004/0081688 A1 | 4/2004 | Del Curto et al. |
| 2004/0115159 A1 | 6/2004 | Tadlock et al. |
| 2004/0115727 A1 | 6/2004 | Steward et al. |
| 2004/0126397 A1 | 7/2004 | Aoki et al. |
| 2004/0127661 A1 | 7/2004 | Kaspar et al. |
| 2004/0132667 A1 | 7/2004 | Lintner |
| 2004/0151741 A1 | 8/2004 | Borodic |
| 2004/0151746 A1 | 8/2004 | Dubief et al. |
| 2004/0191330 A1 | 9/2004 | Keefe et al. |
| 2004/0229038 A1 | 11/2004 | Cooper et al. |
| 2004/0235770 A1 | 11/2004 | Davis et al. |
| 2004/0258747 A1 | 12/2004 | Ponzoni et al. |
| 2004/0258758 A1 | 12/2004 | Gustow et al. |
| 2005/0036966 A1 | 2/2005 | Heckmann |
| 2005/0038096 A1 | 2/2005 | Chow et al. |
| 2005/0048088 A1 | 3/2005 | Zulli et al. |
| 2005/0065090 A1 | 3/2005 | Ludin et al. |
| 2005/0074461 A1 | 4/2005 | Donovan |
| 2005/0074466 A1 | 4/2005 | Suskind et al. |
| 2005/0079131 A1 | 4/2005 | Lanza et al. |
| 2005/0079228 A1 | 4/2005 | Jaiswal et al. |
| 2005/0096340 A1 | 5/2005 | Zhang et al. |
| 2005/0118254 A1 | 6/2005 | Choi et al. |
| 2005/0123897 A1 | 6/2005 | Cevc et al. |
| 2005/0124378 A1 | 6/2005 | Griffith et al. |
| 2005/0136024 A1 | 6/2005 | Stockel |
| 2005/0142150 A1 | 6/2005 | Graham |
| 2005/0147688 A1 | 7/2005 | Russell |
| 2005/0175636 A1 | 8/2005 | Donovan |
| 2005/0184275 A1 | 8/2005 | Mora-Gutierrez et al. |
| 2005/0196414 A1 | 9/2005 | Dake et al. |
| 2005/0196416 A1 | 9/2005 | Kipp et al. |
| 2005/0208083 A1 | 9/2005 | Annis |
| 2005/0214325 A1 | 9/2005 | David |
| 2005/0214378 A1 | 9/2005 | Hoarau et al. |
| 2005/0226842 A1 | 10/2005 | Douin et al. |
| 2005/0249686 A1 | 11/2005 | Pataut et al. |
| 2005/0261632 A1 | 11/2005 | Xu |
| 2006/0018931 A1 | 1/2006 | Taylor |
| 2006/0057165 A1 | 3/2006 | Dimitrakoudis et al. |
| 2006/0073208 A1 | 4/2006 | First |
| 2006/0084353 A1 | 4/2006 | Wong et al. |
| 2006/0093624 A1 | 5/2006 | Graham |
| 2006/0153876 A1 | 7/2006 | Sanders |
| 2006/0153877 A1 | 7/2006 | Kozaki et al. |
| 2006/0165657 A1 | 7/2006 | Bernasconi et al. |
| 2006/0182767 A1 | 8/2006 | Borodic |
| 2006/0182794 A1 | 8/2006 | Modi |
| 2006/0188525 A1 | 8/2006 | Donovan |
| 2007/0009555 A1 | 1/2007 | Borodic |
| 2007/0036831 A1 | 2/2007 | Baker |
| 2007/0104743 A1 | 5/2007 | Lehtola et al. |
| 2007/0116723 A1 | 5/2007 | Coleman |
| 2007/0148194 A1 | 6/2007 | Amiji et al. |
| 2007/0178121 A1 | 8/2007 | First et al. |
| 2007/0253911 A1 | 11/2007 | Tamarkin et al. |
| 2007/0270732 A1 | 11/2007 | Levin et al. |
| 2007/0292359 A1 | 12/2007 | Friedman et al. |
| 2008/0050352 A1 | 2/2008 | Webb et al. |
| 2008/0102089 A1 | 5/2008 | Cappello |
| 2008/0206155 A1 | 8/2008 | Tamarkin et al. |
| 2008/0207737 A1 | 8/2008 | Zinger |
| 2008/0220021 A1 | 9/2008 | Modi |
| 2008/0274195 A1 | 11/2008 | Nicolosi et al. |
| 2009/0041680 A1 | 2/2009 | Tamarkin et al. |
| 2009/0306198 A1 | 12/2009 | Nicolosi et al. |
| 2010/0040883 A1 | 2/2010 | McCarthy et al. |
| 2010/0137357 A1 | 6/2010 | Koleng et al. |
| 2010/0150994 A1 | 6/2010 | Kotyla |
| 2010/0172943 A1 | 7/2010 | Edelson et al. |
| 2010/0183726 A1 | 7/2010 | Nicolosi et al. |
| 2010/0233251 A1 | 9/2010 | Von Andrian et al. |
| 2011/0020227 A1 | 1/2011 | McCarthy et al. |
| 2011/0206736 A1 | 8/2011 | Waldman et al. |
| 2011/0206739 A1 | 8/2011 | Nicolosi et al. |
| 2011/0212157 A1 | 9/2011 | Edelson et al. |
| 2011/0305734 A1 | 12/2011 | Edelson et al. |

(56) References Cited

U.S. PATENT DOCUMENTS

| | | | |
|---|---|---|---|
| 2012/0164182 A1 | 6/2012 | Edelson et al. |
| 2012/0321571 A1 | 12/2012 | Edelson et al. |
| 2012/0321579 A1 | 12/2012 | Edelson et al. |
| 2012/0328525 A1 | 12/2012 | Edelson et al. |
| 2012/0328549 A1 | 12/2012 | Edelson et al. |
| 2012/0328701 A1 | 12/2012 | Edelson et al. |
| 2012/0328702 A1 | 12/2012 | Edelson et al. |
| 2014/0099342 A1 | 4/2014 | Edelson et al. |
| 2014/0234382 A1 | 8/2014 | Edelson et al. |
| 2015/0196490 A1 | 7/2015 | Edelson et al. |
| 2015/0313536 A1 | 11/2015 | Edelson |
| 2015/0313819 A1 | 11/2015 | Edelson |
| 2016/0213757 A1 | 7/2016 | Edelson et al. |
| 2017/0079895 A1 | 3/2017 | Edelson et al. |
| 2017/0087088 A1 | 3/2017 | Edelson et al. |

FOREIGN PATENT DOCUMENTS

| | | |
|---|---|---|
| CA | 2494473 A1 | 4/2005 |
| CA | 2543722 A1 | 5/2005 |
| CA | 2554052 A1 | 8/2005 |
| CA | 2631927 A1 | 4/2008 |
| CA | 2688415 A1 | 12/2008 |
| CN | 1130868 A | 9/1996 |
| DE | 102004016710 A1 | 10/2005 |
| DE | 102006046076 A1 | 4/2007 |
| EP | 0315079 A1 | 5/1989 |
| EP | 0406162 A2 | 1/1991 |
| EP | 0572080 A1 | 12/1993 |
| EP | 0696452 A1 | 2/1996 |
| EP | 0770422 A1 | 5/1997 |
| EP | 1080720 A1 | 3/2001 |
| EP | 1249232 A1 | 10/2002 |
| EP | 1334729 A1 | 8/2003 |
| EP | 1345597 A2 | 9/2003 |
| EP | 1430906 A2 | 6/2004 |
| EP | 1586336 A1 | 10/2005 |
| EP | 1652515 A1 | 5/2006 |
| EP | 1784163 A1 | 5/2007 |
| FR | 2849375 A1 | 7/2004 |
| JP | 1990000203 | 1/1990 |
| JP | 1995285863 | 10/1995 |
| JP | 1996507515 | 8/1996 |
| JP | 2001-513331 A | 9/2001 |
| JP | 2002-308728 A | 10/2002 |
| JP | 2003-527411 A | 9/2003 |
| JP | 2004519447 A | 7/2004 |
| JP | 2004538310 A | 12/2004 |
| JP | 2006273821 A | 10/2006 |
| JP | 2007530544 A | 11/2007 |
| JP | 2008511627 A | 4/2008 |
| JP | 2008514353 A | 5/2008 |
| KR | 20020079150 A | 10/2002 |
| KR | 10-2004-0062602 | 7/2004 |
| WO | WO-1990011364 A1 | 10/1990 |
| WO | WO-9318752 A1 | 9/1993 |
| WO | WO-94/20072 A1 | 9/1994 |
| WO | WO-95/22973 A1 | 8/1995 |
| WO | WO-1995035157 A1 | 12/1995 |
| WO | WO-199639167 A1 | 12/1996 |
| WO | WO-98/51278 A2 | 11/1998 |
| WO | WO-99/07238 A2 | 2/1999 |
| WO | WO-199944594 A1 | 9/1999 |
| WO | WO-200007621 A2 | 2/2000 |
| WO | WO-2000/38653 A1 | 7/2000 |
| WO | WO-200110413 A2 | 2/2001 |
| WO | WO-2001/70197 A2 | 9/2001 |
| WO | WO-200188019 A1 | 11/2001 |
| WO | WO-200239979 A1 | 5/2002 |
| WO | WO-2002/056866 A1 | 7/2002 |
| WO | WO-2002051390 A2 | 7/2002 |
| WO | WO-2002080864 A1 | 10/2002 |
| WO | WO-2003000243 A1 | 1/2003 |
| WO | WO-2003011333 A1 | 2/2003 |
| WO | WO-2003037933 A2 | 5/2003 |
| WO | WO-2003/092585 A2 | 11/2003 |
| WO | WO-2003101483 A1 | 12/2003 |
| WO | WO-2004/006954 A2 | 1/2004 |
| WO | WO-2004/076634 A2 | 9/2004 |
| WO | WO-2004/084839 A2 | 10/2004 |
| WO | WO-2005013938 A1 | 2/2005 |
| WO | WO-2005/020962 A1 | 3/2005 |
| WO | WO-2005/027872 A1 | 3/2005 |
| WO | WO-2005023282 A1 | 3/2005 |
| WO | WO-2005042539 A1 | 5/2005 |
| WO | WO-2005058370 A1 | 6/2005 |
| WO | WO-2005063377 A1 | 7/2005 |
| WO | WO-2005070394 A2 | 8/2005 |
| WO | WO-2005082514 A2 | 9/2005 |
| WO | WO-2005084361 A2 | 9/2005 |
| WO | WO-2005091991 A2 | 10/2005 |
| WO | WO-2005102285 A1 | 11/2005 |
| WO | WO-2006/005910 A2 | 1/2006 |
| WO | WO-2006025976 A1 | 3/2006 |
| WO | WO-2006028339 A1 | 3/2006 |
| WO | WO-2006039014 A1 | 4/2006 |
| WO | WO-2006/050926 A2 | 5/2006 |
| WO | WO-2006/084353 A1 | 8/2006 |
| WO | WO-2006/094263 A2 | 9/2006 |
| WO | WO-2006123354 A2 | 11/2006 |
| WO | WO-2006138127 A2 | 12/2006 |
| WO | WO-2007/041664 A1 | 4/2007 |
| WO | WO-2007046102 A2 | 4/2007 |
| WO | WO-2007/089454 A2 | 8/2007 |
| WO | WO-2007/103555 A2 | 9/2007 |
| WO | WO-2007149868 A2 | 12/2007 |
| WO | WO-2008010788 A2 | 1/2008 |
| WO | WO-2008038147 A2 | 4/2008 |
| WO | WO-2008045107 A2 | 4/2008 |
| WO | WO-2008070538 A2 | 6/2008 |
| WO | WO-2008074885 A2 | 6/2008 |
| WO | WO-2008077641 A1 | 7/2008 |
| WO | WO-2008140594 A2 | 11/2008 |
| WO | WO-2008151022 A2 | 12/2008 |
| WO | WO-2009158687 A1 | 12/2009 |
| WO | WO-2010087964 A2 | 8/2010 |

OTHER PUBLICATIONS

Badea et al., In vivo cutaneous interferon-γ, gene delivery using novel dicationic (gemini) surfactant-plasmid complexes, J Gene Medicine 7:1200-1214 (2005).

Badea et al., In vivo cutaneous interferon-.gamma. gene delivery using novel dicationic (gemini) surfactant-plasmid complexes, J Gene Medicine 7:1200-1214 (2005).

Barr et al., Different Substrate Recognition Requirements for cleavage of Synaptobrevin-2 by Clostridium baratii and Clostridium botulinum, Applied and Environmental Microbiology p. 1301-1308, 2011.

Bauerova et al., Chemical enhancers for transdermal drug transport, European J Drug Metabolism and Pharmacokinetics 26(1/2):85-94 (2001).

Bhartiya et al., Enhanced Wound Healing in Animal Models by Interferon and an Interferon Inducer, J Cell Physio1150:312 (1992).

Bhartiya et al., Enhanced Wound Healing in Animal Models by Interferon and an Interferon Inducer, J Cell Physiol 150:312-319 (1992).

Bos and Meinardi, The 500 Dalton rule for the skin penetration of chemical compounds and drugs, Exp Dermatol 9:165-169 (2000).

Brewster, Delivering Anti-aging Actives, Cosmetics and Toiletries, 120(6):30, 32-34 (2005).

Carruthers et al., Botulinum A exotoxin use in clinical dermatology, J. Am. Acad. Dermatol. 34(5):788 (1996).

Chen et al., Transdermal protein delivery by a coadministered peptide identified via phage display, Nature Biotechnology 24(4):455-459 (2006).

Choi et al, Percutaneous Absorption, Fourth Edition Bronaugh and Maibach ed., Taylor and Francis, Boca Ratonm Florida, Index and Table of contents only 155:33 (2005).

Cocconi et al., Treatment of Metastatic Malignant Melanoma with Dacarbazine Plux Tamoxifen, New England J Medicine 327(8):516-23 (1992).

(56) References Cited

OTHER PUBLICATIONS

Croda Inc., Pharmaceutical Technology, 3 pages (2005), Retrieved online: http://www.pharmtech.com/pharmtech/Corporate=Capabilities/Croda-Inc/Artic-leStandard/Article/detail/399061.
Dalgleish et al., The characterization of small emulsion droplets made from milk proteins and triglyceride oil, Colloids and Surfaces, 123-124:145-153 (May 15, 1997).
De Campo et al., Five-component food-grade microemulsions: Structural characterization by Sans, J Colloid and Interface Science, 274:251-267 (2004).
De Paiva and Dolly, Light chain of botulinum nerotoxin is active in mammalian motor nerve terminals when delivered via liposomes, FEBS 277(1,2):171-174 (1990).
Delgado-Charro et al., Delivery of a hydrophilic solute through the skin from novel microemulsion systems, Eur J Pharmaceutics and Biopharmaceutics 43[1]:37-42 (1997).
Examination Report for EP 06851782.0, 7 pages (dated Jun. 3, 2014).
Examination Report for EP 07874325.9, 8 pages (dated Apr. 5, 2012).
Examination Report for EP 12702700.1, 6 pages (dated Aug. 21, 2014).
Examination Report for SG 200903663-3, 4 pages (dated Oct. 11, 2011).
Extended European Search Report for EP 09724172.3, 8 pages (dated Dec. 13, 2013).
Extended European Search Report for EP 12160402.9, 4 pages (dated Aug. 6, 2012).
Extended European Search Report for EP07861297.5, 4 pages (dated Apr. 7, 2010).
Freitas et al. (European Journal of Pharmaceutics and Bopharmaceutics 1998;46:145-151).
Garcion et al., A New Generation of Anticancer, Drug-loaded, Colloidal Vectors Reverses Multidrug Resistance in Glioma and Reduces Tumor Progression in Rats, Mol. Cancer Ther., 1710-1722 (2006).
Hancock et al., An Antioxidant Formulation that Induces Differentiation of Neuroblastoma in Culture, Neuroscience Research Communications, 33(1): 73-76 (2003).
Helene et al., Control of Gene Expression by Triple Helix-Forming Oligonucleotides, Ann N.Y. Acad Sci 660:27-36 (1992).
Helene, The anti-gene strategy: control of gene expression by triplex-forming-oligonucleotides, Anti-Cancer Drug Des 6:569-584 (1991).
Heurtault et al., A Novel Phase Inversion-Based Process for the Preparation of Lipid Nanocarriers, Pharmaceutical Research 19(6):875-880 (2002).
Hickerson et al., SiRNA-Mediated Selective Inhibition of Mutant Keratin mRNAs Responsible for the Skin Disorder Pachyonychia Congenita, Ann. N.Y. Acad. Sci. 1082:56-61 (2006).
International Preliminary Report on Patentability for PCT/US2006/035343, 5 pages (dated Mar. 18, 2008).
International Preliminary Report on Patentability for PCT/US2007/010253, 5 pages (dated Oct. 28, 2008).
International Preliminary Report on Patentability for PCT/US2007/086018, 7 pages (dated Jun. 3, 2009).
International Preliminary Report on Patentability for PCT/US2007/086040, 13 pages (dated Feb. 16, 2010).
International Preliminary Report on Patentability for PCT/US2008/065329, 8 pages (dated Dec. 1, 2009).
International Preliminary Report on Patentability for PCT/US2009/048972, 6 pages (dated Jan. 5, 2011).
International Preliminary Report on Patentability for PCT/US2012/022276, 10 pages (dated Aug. 8, 2013).
International Preliminary Report on Patentability for PCT/US2012/022277, 7 pages (dated Aug. 8, 2013).
International Preliminary Report on Patentability for PCT/US2012/022278, 8 pages (dated Aug. 8, 2013).
International Preliminary Report on Patentability for PCT/US2012/022279, 9 pages (dated Aug. 8, 2013).
International Preliminary Report on Patentability for PCT/US2012/022280, 8 pages (dated Aug. 8, 2013).
International Preliminary Report on Patentability for PCT/US2012/022281, 7 pages (dated Aug. 8, 2013).
International Search Report for PCT/US2006/026918, 4 pages (dated Jun. 19, 2008).
International Search Report for PCT/US2006/035343, 1 page (dated Aug. 15, 2007).
International Search Report for PCT/US2006/046236, 3 pages (dated Jun. 17, 2008).
International Search Report for PCT/US2007/010253, 3 pages (dated Mar. 14, 2008).
International Search Report for PCT/US2007/086018, 5 pages (dated Sep. 17, 2008).
International Search Report for PCT/US2007/086040, 7 pages (dated Feb. 9, 2010).
International Search Report for PCT/US2008/065329, 5 pages (dated Mar. 12, 2009).
International Search Report for PCT/US2009/048972, 5 pages (dated Dec. 1, 2009).
International Search Report for PCT/US2012/022276, 6 pages (dated Jul. 19, 2012).
International Search Report for PCT/US2012/022277, 4 pages (dated Jul. 6, 2012).
International Search Report for PCT/US2012/022278, 4 pages (dated Mar. 23, 2012).
International Search Report for PCT/US2012/022279, 7 pages (dated Nov. 29, 2012).
International Search Report for PCT/US2012/022280, 4 pages (dated Apr. 27, 2012).
International Search Report for PCT/US2012/022281, 4 pages (dated Apr. 24, 2012).
Izquierdo et al., The influence of surfactant mixing ration on nano-emulsion formation by the pit method, J Colloid and Interface Sci. 285:388-394 (2004).
Johnson et al., Clostridium botulinum neurotoxins—Applications in Medicine and Potential Agents of Bioterrorism, Clinical Microbiology Newsletter, 27(19):147-151 (2005).
Kakumanu et al., A Nanoemulsion Formulation of Dacarbazine Reduces Tumor Size in a Xenograft Mouse Epidermoid Carcinoma Model Compared to Dacarbazine Suspension, Nanomedicine: NBM 7(3):277-283 (2011).
Kalb et al, Different Substrate Recognition Requirements for cleavage of Synaptobrevin-2 by Clostridium baratii and Clostridium botulinum Type F Neurotoxins, Applied and Environmental Microbiology, 77(4):1301-1308 (2011).
Katayama et al., A Pentapeptide from Type I Procollagen Promotes Extracellular Matrix Production, J Biol Chem 268(14):9941-9944 (1993).
Keen et al., Botulinum Toxin A for Hyperkinetic Facial Lines: Results of a Double-Blind, Placebo-Controlled Study, Plastic and Reconstructive Surgery, 94(1):94-9 (1994).
Kitson, Drugs Used for Skin Diseases, Published in Dermatologic, Cosmeceutic, and Cosmetic Development Therapeutic and Novel Approaches, Ed Walters and Roberts 11-20 (2008).
Kotyla et al., Increased bioavailability of a transdermal application of a nano-sized emulsion preparation, International Journal of Pharmaceutics 347:144-148 (2008).
Kronberg et al., Preparation and Evaluation of Sterically Stabilized Liposomes: Colloidal Stability, Serum Stability, Macrophage Uptake, and Toxicity, J Pharmaceutical Sciences 79(8):667-671 (1990).
Kuo et al., Nanomulsions of an Anti-Oxidant Synergy Formulation Containing Gamma Tocopherol Have Enhanced Bioavailability and Anti-Inflammatory Properties, Int'l J Pharmaceutics 363:206-213 (2008).
Lin et al., Delivery of plasmid DNA expression vector for keratinocyte growth factor-1 using electroporation to improve cutaneous wound healing in a septic rat model, Wound Repair and Regenertion 14:618-624 (2006).
Ludewig and Hoffmann, Adoptive Immunotherapy Methods and Protocols, Humana Press Inc., NJ 393 (2005).
Lupo, Cosmeceutical Peptides, Dermatologic Surgery 31:832-836 (2005).

(56) References Cited

OTHER PUBLICATIONS

Maher, DNA Triple-Helix Formation: An Approach to Artificial Gene Repressors?, BioEssays 14:807-815 (1992).
Montecucco et al., Effect of pH on the interaction of botulinum neurotoxins A, B and E with liposomes, Biochem J 259:47-53 (1989).
Morel et al., Incorporation in liposheres of {D-Trp-6}LHRH, Int'l J Pharmaceutics 105(2):R01-R03 (1994).
Muller, R.H. et al., Solid lipid nanoparticles (SLN) for controlled drug delivery—a review of the state of the art. European Journal of Pharmaceutics and Biopharmaceutics, 50(1):161-77 (2000).
Notice of Final Rejection for JP2011-516743, 4 pages (dated Jul. 28, 2014).
Official Action for Mexican Patent Application No. MX/a/2010/013562, 2 pages (dated Dec. 17, 2013).
Official Action for Mexican Patent Application No. MX/a/2010/013562, 2 pages (dated Jun. 11, 2014).
Official Action for Patent Application No. 2011-516743, 11 pages (dated Oct. 4, 2013).
Pearce et al., Pharmacologic Characterization of Botulinum Toxin for Basic Science and Medicine, Toxicon 35(9):1373-1412 (1997).
Poste et al., Lipid Vesicles as Carriers for Introducing Biologically Active Materials into Cells, Methods in cell biology 14:34-35 (1976).
PTO892 mailed Dec. 11, 2012, 1 page.
PTO892, 1 page (Feb. 19, 2013).
Robinson, et al., Topical palmitoyl pentapeptide provides improvement in photoaged human facial skin, Int'l J Cosmetic Science 24:155-160 (2005).
Santiago et al., Topical Application of a Peptide Inhibitor of Transforming Growth Factor-.beta.1 Ameliorates Bleomycin-Induced Skin Fibrosis, J Investigative Dermatorlogy 125:450-455 (2005).
Sarver et al., Ribozymes as Potential Anti-HIV-1 Therapeutic Agents, Science 247:1222-1225 (1990).
Schantz et al, Properties and use of botulinum toxin and other microbial neurotoxins in medicine, Microbiol. Mol. Biol. Rev., 80-99 (1992).
Schmalfu.beta. et al., Modification of drug penetration into human skin using microemulsions, J Controlled Release 46(3):279-285 (1997).
Search Report for AU2007329579, 3 pages (dated Jun. 1, 2012).
Search Report for AU2007353340, 2 pages (dated May 28, 2012).
Search Report for SG 200903662-5, 8 pages (dated Oct. 29, 2010).
Search Report for SG 200903663-3, 8 pages (dated Oct. 12, 2010).
Shea et al., Efficacy of Vitamin E, Phosphatidyl Choline, and Pyruvate on Buffering Neuronal Degeneration and Oxidative Stress in Cultured Cortical Neurons and in Central Nervous Tissue of Apolipoprotein E-Deficient Mice, Free Radical Biology &Medicine 33:(2):276-282 (2002).
Shone et al., A 50-kDa fragment from the NH.sub.2-terminus of the heavy subunit of Clostridium botulinum type A neurotoxin forms channels in lipid vesicles, Eur J Biochem 167:175-180 (1987).
Supplementary European Search Report for Application No. EP06851782, 10 pages, dated Jul. 3, 2012.
Supplementary European Search Report for EP06851414.0, 8 pages (dated Oct. 1, 2012).
Tadros et al., Formation and stability of nano-emulsions, Advances in Colloid and Interface Science 108:109-303-318 (2004).
Tagne et al., Nanoemulsion Preparations of the Anticancer Drug Dacarbazine Significantly Increase Its Efficacy in Xenograft Mouse Melanoma Model, Molecular Pharmaceutics 5(6):1055-1063 (2008).
The Harley Medical Group, Excessive Sweating—Causes and Treatment, <http://www.harleymedical.co.uk/non-surgical-solutions/causes/excessiv- e-sweating/> 1 page [last accessed Aug. 26, 2013].
Trotta et al., Elastic Liposomes for Skin Delivery of Dipotassium Glycyrrhizinate, Int'l J Pharmaceutics 241:319-327 (2002).
Verma et al., Particle size of liposomes influences dermal delivery of substances into skin, Int'l J Pharmaceutics 141-151 (2003).
Wang et al., Enhancing effect of Labrafac Lipophile WL 1349 on oral bioavailability of hydroxysafflor yellow A in rats, International Journal of Pharmaceutics 358:198-204 (2008).
Written Opinion for PCT/US2007/010253, 4 pages (dated Mar. 14, 2008).
Written Opinion for PCT/US2007/086018, 6 pages (dated Sep. 17, 2008).
Written Opinion for PCT/US2007/086040, 12 pages (dated Feb. 9, 2010).
Written Opinion for PCT/US2008/065329, 7 pages (dated Mar. 12, 2009).
Written Opinion for PCT/US2009/048972, 5 pages (dated Dec. 1, 2009).
Written Opinion for PCT/US2012/022276, 9 pages (dated Jul. 19, 2012).
Written Opinion for PCT/US2012/022277, 6 pages (dated Jul. 6, 2012).
Written Opinion for PCT/US2012/022279, 7 pages (dated Nov. 29, 2012).
Written Opinion for PCT/US2012/022280, 7 pages (dated Apr. 27, 2012).
Written Opinion for PCT/US2012/022281, 6 pages (dated Apr. 24, 2012).
Written Opinion for PCT/US20120/22278, 7 pages (dated Mar. 23, 2012).
Written Opinion for SG 200903663-3, 7 pages (dated Oct. 12, 2010).
Written Opinion for SG 201009039-7, 6 pages (dated Mar. 12, 2012).
Written Opinion for SG200903662-5, 4 pages (dated Oct. 29, 2010).
Wu et al., Topical Transfection Using Plasmid DNA in a Water-in-Oil Nanoemulsion, Int J Pharmceutics 221(1/02):23-34 (2001).
Wu et al., Topical Transport of Hydrophilic Compounds Using Water-in-Oil Nanoemulsions, Int. J. Pharmaceutics, 220:63-75 (2001).
Unpublished, U.S. Appl. No. 16/164,395, filed Oct. 18, 2018, 212 pages.
U.S. Appl. No. 11/741,125, filed Apr. 27, 2007, US 2007/0259391, Issued as U.S. Pat. No. 8,658,391.
U.S. Appl. No. 12/517,154, filed Feb. 24, 2010, US 2010/0150994, Abandoned.
U.S. Appl. No. 14/182,919, filed Feb. 18, 2014, US 2014/0161854, Issued as U.S. Pat. No. 9,724,299.
U.S. Appl. No. 12/517,149, filed Mar. 1, 2010, US 2010/0172943, Abandoned.
U.S. Appl. No. 14/187,246, filed Feb. 22, 2014, US 2014/0234382, Issued as U.S. Pat. No. 9,486,409.
U.S. Appl. No. 15/279,687, filed Sep. 29, 2016, US 2017/0079895, Pending.
U.S. Appl. No. 12/671,693, filed May 6, 2011, US 2011/0305734, Allowed.
U.S. Appl. No. 13/000,509, filed May 6, 2011, US 2011/0212157, Abandoned.
U.S. Appl. No. 14/836,076, filed Aug. 26, 2015, US 2016/0213757, Pending.
U.S. Appl. No. 13/356,621, filed Jan. 23, 2012, US 2012/0328702, Abandoned.
U.S. Appl. No. 14/598,764, filed Jan. 16, 2015, US 2015/0196490, Abandoned.
U.S. Appl. No. 13/356,623, filed Jan. 23, 2012, US 2012/0328525, Abandoned.
U.S. Appl. No. 15/378,561, filed Dec. 14, 2016, US 2017/0087088, Abandoned.
U.S. Appl. No. 13/356,634, filed Jan. 23, 2012, US 2012/0328549, Abandoned.
U.S. Appl. No. 13/356,617, filed Jan. 23, 2012, US 2012/0328701, Pending.
U.S. Appl. No. 16/164,395, filed Oct. 18, 2018, Unpublished, Pending.
U.S. Appl. No. 13/356,629, filed Jan. 23, 2012, US 2012/0321579, Abandoned.
U.S. Appl. No. 13/356,627, filed Jan. 23, 2012, US 2012/0321571, Abandoned.

(56) References Cited

OTHER PUBLICATIONS

U.S. Appl. No. 14/702,269, filed May 1, 2015, US 2015/0313536, Pending.
U.S. Appl. No. 14/702,256, filed May 1, 2015, US 2015/0313819, Issued as U.S. Pat. No. 9,649,266.

AMPHIPHILIC ENTITY NANOPARTICLES

RELATED APPLICATIONS

This application is a continuation of U.S. patent application Ser. No. 14/182,919, filed Feb. 18, 2014, which is a continuation of U.S. patent application Ser. No. 12/517,154, filed Feb. 24, 2010, which is a 35 U.S.C. § 371 National Stage of International Application No. PCT/US07/86018, filed Nov. 30, 2007, which claims priority under 35 U.S.C. § 119(e) to U.S. provisional patent application, U.S. Ser. No. 60/872,198, filed Dec. 1, 2006. The entire contents each of the foregoing applications are incorporated herein by reference.

BACKGROUND OF THE INVENTION

A significant literature exists on strategies for producing polymer nanoparticles. For example, when an amphiphilic polymer is present in a solvent at a concentration above its critical micellar concentration, it will self-assemble into nanoparticle structures. Even when such a polymer is present at a lower concentration, it can be caused to form nanoparticles by decreasing the solvation of the solvent such as by diluting the solvent with water. Solvents that have traditionally been used to manufacture nanoparticles were usually one or more of dimethyl sulfoxide (DMSO), dimethyl acetimide, dimethyl formamide, chloroform, tetramethyl formamide. Unfortunately, each of these is highly toxic and expensive.

In addition to the fact that they require one or more toxic solvents, standard methods for generating polymer nanoparticles tend to be slow (requiring up to several days to complete nanoparticle assembly), and to give only low yields of nanoparticles. Thus, the cost of the components, the speed and yield of the chemical reaction, the toxicity of the residual components, and the overall expense of the available processes for producing nanoparticles can have a profound negative impact on the commercial feasibility of using such nanoparticles.

Nanoparticles are often proposed for use as a delivery mechanism for a biologically active agent, such as a pharmaceutical. Frequently, it has been challenging to incorporate (or "load") the biologically active agent into the nanoparticle because the amount that can be incorporated is limited or that it takes a great deal of time to incorporate the material (through, for example, diffusion). This challenge can limit the practical or commercial utility of the nanoparticle as a delivery mechanism for a biologically active agent.

Therefore, there is a need for the development of inexpensive, efficient methods of manufacturing nanoparticles. There is a further need for the development of methods of manufacturing nanoparticles that do not utilize or leave behind toxic residual components or reaction by-products.

SUMMARY OF THE INVENTION

In some embodiments, the present invention provides nanoparticle compositions comprising amphiphilic entity (AE) nanoparticles. In some embodiments, the nanoparticle compositions are uniform. For example, in some embodiments, the total particle distribution is encompassed within a particular range of particle diameter sizes (discussed in more detail below); in some embodiments, a portion of the total particle distribution is outside of the particular range.

In some embodiments, the present invention provides AE nanoparticles and pharmaceutical compositions comprising AE nanoparticles. In some embodiments, AE nanoparticles comprise one or more amphiphilic entities. The AE nanoparticles may comprise one or more dispersion media, surfactants, biologically active agents, and/or release-retarding ingredients. In some embodiments, the AE nanoparticles are smaller than 1000 nanometers, 500 nanometers, 200 nanometers, or 100 nanometers in diameter.

In some embodiments, the present invention provides systems, including methods, reagents, and/or compositions, for manufacturing AE nanoparticles. In some embodiments, AE nanoparticle compositions may be generated by exposure to high shear forces; in some embodiments, AE nanoparticle compositions may be generated high pressure homogenization; in some embodiments, AE nanoparticle compositions may be generated by cavitation; in some embodiments, AE nanoparticle compositions may be generated by microfluidization. In some embodiments, commercially available equipment, such the Microfluizider®, may be used to generate high shear forces.

In some embodiments, methods of manufacturing AE nanoparticles generally comprise steps of preparing a premix of one or more amphiphilic entities and applying high shear force to the premix. The premix generally contains one or ore amphiphilic entities and one ore more dispersion media. The premix may optionally comprise one or more surfactants, biologically active agents, and/or release-retarding ingredients. In some embodiments, the amphiphilic entities of the premix assemble into particles (e.g. nanoparticles, microparticles, and/or micelles) before application of high shear force. In some embodiments, the amphiphilic entities of the premix do not assemble into particles before the application of high shear force.

In some embodiments, the present invention provides improvements over traditional methods of manufacturing nanoparticles. For example, the use of mechanical energy replaces or minimizes the requirement to use costly and toxic chemical solvents, increases the speed and reaction yield, reduces the overall cost of the synthetic reaction, thereby increasing the commercial utility of AE nanoparticles. Additionally, the use of high shear force allows for increased loading capacity of the nanoparticle as compared to traditional methods of forming nanoparticles. In traditional methods, loading of agents within or on the surface of nanoparticles relies on diffusion of the agent to the interior and/or to the surface of the nanoparticle.

The present invention encompasses the recognition that subjecting particles (e.g. nanoparticles, microparticles, and/or micelles) to high shear force is a method of manufacturing nanoparticles that is inexpensive and efficient and does not utilize toxic residual components. In some embodiments, the AE nanoparticles are completely free or substantially free of toxic components. In some embodiments, the nanoparticle compositions comprising AE nanoparticles are completely free or substantially free of toxic components. The present invention further encompasses the recognition that subjecting particles (e.g. nanoparticles, microparticles, and/or micelles) to high shear force generates nanoparticles with an increased loading capacity relative to traditional methods of making nanoparticles.

In some embodiments, the present invention provides a method of delivering a composition, substance, or biologically active agent to a subject. In some embodiments, the composition, substance, or biologically active agent may be delivered via any route. In some embodiments, the composition, substance, or biologically active agent is delivered transdermally (or topically).

In some embodiments, the invention provides methods and compositions for transdermally delivering a biologically active agent to a subject by administering to the subject nanoparticle compositions comprising AE nanoparticles to the surface of the subject's skin, wherein the biologically active agent is encapsulated within and/or bound to the surface of the AE nanoparticles. The present invention encompasses the discovery that AE nanoparticles of the present invention can achieve transdermal delivery of a biologically active agent without changing or altering the structure of the skin. For example, abrasive agents or agents that erode the top layer of the skin (whether chemical, mechanical, electrical, magnetic, etc.) are not required to achieve transdermal delivery of a biologically active agent. In some embodiments, a composition for transdermal delivery of a biologically active agent may be in the form of a transdermal patch. In some embodiments, inventive compositions comprising AE nanoparticles for transdermal delivery of a biologically active agent may be used in an application device that permits application of the composition to a target site on the skin without applying the composition to non-target site areas of the skin.

In some embodiments, the biologically active agent comprises a biological polymer. In some embodiments, the polymer is DNA, RNA, or a protein. In some embodiments, the protein comprises multiple proteins and/or protein complexes. In certain embodiments, the biologically active agent delivered according to the present invention is one or more botulinum toxin peptides, polypeptides and/or protein complexes. In some embodiments, the botulinum toxin may be one or more of botulinum toxin serotypes A, B, $C_1$, $C_2$, D, E, F, or G. In some embodiments, the botulinum toxin may be an isolated and/or purified botulinum toxin. In some embodiments, the botulinum toxin may be a partially-isolated and/or partially-purified botulinum toxin. In some embodiments, the botulinum toxin may be a native botulinum complex. In some embodiments, the botulinum toxin may be associated with non-toxin proteins. In some embodiments, the botulinum toxin may be a recombinantly-made botulinum toxin.

In some embodiments, the present invention provides methods of treating facial wrinkles (e.g. wrinkles involving the forehead, glabellar, rhytids, and/or periorbital regions); hyperkinetic facial lines; platysma bands; neuromuscular disorders and conditions involving muscular spasm and/or contracture (e.g. facial palsy, blepharospasm, cerebral palsy, strabismus, and/or dystonia); prostate hyperplasia; hyperhidrosis; headache, and/or temporomandibular joint diseases and disorders (TMJ, also known as "lockjaw"). Such methods generally involve administering to a subject nanoparticle compositions comprising AE nanoparticles for the transdermal delivery of a botulinum toxin or botulinum toxin complex.

In some embodiments, the present invention provides methods of treating facial wrinkles (e.g. wrinkles involving the forehead, glabellar, rhytids, and/or periorbital regions), hyperkinetic facial lines, and/or platysma bands. In some embodiments, nanoparticle compositions comprising AE nanoparticles for the transdermal delivery of a biologically active agent may be used to treat facial wrinkles. In some embodiments, nanoparticle compositions comprising AE nanoparticles for the transdermal delivery of a botulinum toxin or botulinum toxin complex may be used to treat facial wrinkles. In some embodiments, facial wrinkles may include glabellar wrinkles, facial lines (e.g. hyperkinetic facial lines), forehead frown lines, midfacial wrinkles, mouth wrinkles, neck lines and banding (e.g. platysma bands), and chin creases. Such methods generally involve administering to a subject nanoparticle compositions comprising AE nanoparticles for the transdermal delivery of a botulinum toxin or botulinum toxin complex.

In some embodiments, the present invention does not provide methods of treating prostate hyperplasia. In some embodiments, the present invention does not provide methods of treating neuromuscular disorders and conditions involving muscular spasm and/or contracture. In some embodiments, the present invention does not provide methods of treating hyperhidrosis. In some embodiments, the present invention does not provide methods of treating headache. In some embodiments, the present invention does not provide methods of treating TMJ.

This application refers to various patent publications, all of which are incorporated herein by reference.

Definitions

Abrasion: The term "abrasion," as used herein refers to any means of altering, disrupting, removing, or destroying the top layer of the skin. In some embodiments, abrasion refers to a mechanical means of altering, disrupting, removing, or destroying the top layer of the skin. In some embodiments, abrasion refers to a chemical means of altering, disrupting, removing, or destroying the top layer of skin. To give but a few examples, agents such as exfoliants, fine particles (e.g. magnesium or aluminum particles), acids (e.g. alpha-hydroxy acids or beta-hydroxy acids), alcohols, may cause abrasion. In general, permeation enhancers such as those described, for example, by Donovan (e.g. U.S. Patent Publications 2004/009180 and 2005/175636 and PCT Publication WO 04/06954; all of which are incorporated herein by reference), and Graham (e.g. U.S. Pat. No. 6,939,852 and U.S. Patent Publication 2006/093624; both of which are incorporated herein by reference), etc., are expected to cause abrasion. Of course, those of ordinary skill in the art will appreciate that a particular agent may cause abrasion when present at one concentration, or in association with one or more other agents, but may not cause abrasion under different circumstances. Thus, whether or not a particular material is an "abrasive agent" depends on context. Abrasion can readily be assessed by those of ordinary skill in the art, for example by observation of redness or irritation of the skin and/or histologic examination of skin showing alteration, disruption, removal, or erosion of the stratum corneum.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions Amino acids, including carboxy- and/or amino-terminal amino acids in peptides, can be modified by methylation, amidation, acetylation, and/or substitution with other chemical groups that can change the peptide's circulating half-life without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Amphiphilic entity: As used herein, the term "amphiphilic entity" refers to a chemical entity possessing both hydrophilic and hydrophobic nature. As used herein, the terms "amphiphilic" and "amphipathic" can be used interchangeably. In some embodiments, the amphiphilic entities of an AE nanoparticle are biocompatible. Biocompatible amphiphilic entities are not significantly toxic to cells. In some embodiments, the amphiphilic entities of an AE nanoparticle are biodegradable. Biodegradable amphiphilic entities are broken down by the cellular machinery and/or by hydrolysis into components that the cells can either reuse or dispose of without significant toxic effect. In some embodiments, a biodegradable amphiphilic entity and its biodegradation byproducts are biocompatible. In some embodiments, the amphiphilic entity is non-immunogenic. In some embodiments, an amphiphilic entity may comprise one or more individual compounds or molecules that is itself amphiphilic. In some embodiments, an amphiphilic entity may comprise one or more individual components that is not itself amphiphilic but that has some hydrophilic or hydrophobic character. Typically, the individual components are associated with one another such that the assemblage of the individual components is amphiphilic.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Antibody: As used herein, the term "antibody" refers to an immunoglobulin, whether naturally produced, synthetically produced, or both. The antibody may be a member of any immunoglobulin class, including any of the human classes: IgG, IgM, IgA, IgD, and/or IgE. The antibody may be a fragment of an antibody such as an Fab'; F(ab')$_2$; scFv (single-chain variable) and/or any other fragment that retains an antigen binding site; and/or a recombinantly-produced scFv fragment, including recombinantly-produced fragments (see, e.g., Allen, 2002, *Nat Rev Cancer*, 2:750 and references therein; incorporated herein by reference). In certain embodiments of the invention the term refers to "humanized" antibodies, which include sequences of human origin. In some embodiments, "humanized" antibodies are characterized by a variable domain of rodent origin fused to a constant domain of human origin, thus retaining the specificity of the rodent antibody. It is noted that the domain of human origin need not originate directly from a human in the sense that it is first synthesized in a human being. For example, "human" domains may be generated in rodents whose genome incorporates human immunoglobulin genes (see, e.g., Harlow et al., *Antibodies: A Laboratory Manual*, Cold Spring Harbor Laboratory Press, Cold Spring Harbor, N.Y., 1988; incorporated herein by reference). An antibody may be polyclonal or monoclonal.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active agent: As used herein, the phrase "biologically active agent" refers to any substance that has activity in a biological system and/or organism. For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the phrase a "characteristic portion" of a substance, in the broadest sense, is one that shares some degree of sequence and/or structural identity and/or at least one functional characteristic with the relevant intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally will contain at least 2, 5, 10, 15, 20 or more amino acids. In general, a characteristic portion is one that, in addition to the sequence identity specified above, shares at least one functional characteristic with the relevant intact protein. In some embodiments, the characteristic portion may be biologically active.

Dispersion medium: The term "dispersion medium," as used herein, refers to a liquid medium in which particles (e.g., AE nanoparticles) are dispersed. In general, a dispersion is formed when at least two immiscible materials are combined. An "oil-in-water" dispersion is one in which oily particles are dispersed within an aqueous dispersion medium. A "water-in-oil" dispersion is one in which aqueous particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories.

Encapsulated: The term "encapsulated" (also "encapsulate" or "encapsulating") is used herein to mean that the encapsulated entity is completely surrounded by another material. To give but one example, a biologically active agent may be encapsulated within a nanoparticle in an inventive composition. Such encapsulation may be achieved, for example, during formation of a nanoparticle composition, for example during exposure to high shear force.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; (4) post-translational modification of a polypeptide or protein.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the terms "homology" and "identity" are used interchangeably and refer to the overall relatedness between polymeric molecules, e.g. between nucleic acid molecules (e.g. DNA molecules and/or RNA molecules) and/or between polypeptide molecules. Calculation of the percent homology or identity of two nucleic acid sequences can be performed by aligning the two sequences for optimal comparison purposes (e.g., gaps can be introduced in one or both of a first and a second nucleic acid sequences for optimal alignment and non-homologous sequences can be disregarded for comparison purposes). In certain embodiments, the length of a sequence aligned for comparison purposes is at least 30%, at least 40%, at least 50%, at least 60%, at least 70%, at least 80%, at least 90%, at least 95% or 100% of the length of the reference sequence. Nucleotides at corresponding nucleotide positions are then compared. When a position in the first sequence is occupied by the same nucleotide as the corresponding position in the second sequence, then the molecules are identical (or homologous) at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17; incorporated herein by reference), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Hydrophilic: As used herein, a "hydrophilic" substance is a substance that may be soluble in polar dispersion media. In some embodiments, a hydrophilic substance can transiently bond with polar dispersion media. In some embodiments, a hydrophilic substance transiently bonds with polar dispersion media through hydrogen bonding. In some embodiments, the polar dispersion medium is water. In some embodiments, a hydrophilic substance may be ionic. In some embodiments, a hydrophilic substance may be non-ionic. In some embodiments, a hydrophilic substance may dissolve more readily in water, polar dispersion media, or hydrophilic dispersion media than in oil, non-polar dispersion media, or hydrophobic dispersion media. In some embodiments, a hydrophilic substance may dissolve less readily in oil, non-polar dispersion media, or hydrophobic dispersion media than in water, polar dispersion media, or hydrophilic dispersion media. In some embodiments, a substance is hydrophilic relative to another substance because it is more soluble in water, polar dispersion media, or hydrophilic dispersion media than is the other substance. In some embodiments, a substance is hydrophilic relative to another substance because it is less soluble in oil, non-polar dispersion media, or hydrophobic dispersion media than is the other substance.

Hydrophobic: As used herein, a "hydrophobic" substance is a substance that may be soluble in non-polar dispersion media. In some embodiments, a hydrophobic substance is repelled from polar dispersion media. In some embodiments, the polar dispersion medium is water. In some embodiments, hydrophobic substances are non-polar. In some embodiments, a hydrophobic substance may dissolve more readily in oil, non-polar dispersion media, or hydrophobic dispersion media than in water, polar dispersion media, or hydrophilic dispersion media. In some embodiments, a hydrophobic substance may dissolve less readily in water, polar dispersion media, or hydrophilic dispersion media than in oil, non-polar dispersion media, or hydrophobic dispersion media. In some embodiments, a substance is hydrophobic relative to another substance because it is more soluble in oil, non-polar dispersion media, or hydrophobic dispersion media than is the other substance. In some embodiments, a substance is hydrophobic relative to another substance because it is less soluble in water, polar dispersion media, or hydrophilic dispersion media than is the other substance.

In conjunction with: As used herein, the phrase "delivered in conjunction with" refers to the co-delivery of two or more substances or agents. In particular, according to the present invention, the phrase is used herein in reference to delivery of a biologically active agent with inventive AE nanoparticles and/or nanoparticle compositions. A substance or agent is delivered in conjunction with AE nanoparticles when the substance or agent is combined with AE nanoparticles and/or nanoparticle compositions; is encapsulated or completely surrounded by AE nanoparticles; is embedded within an AE nanoparticle micellar membrane; and/or is associated with the outer surface of an AE nanoparticle micellar membrane. A substance or agent to be delivered in conjunction with AE nanoparticles and/or nanoparticle compositions may or may not be covalently linked to the AE nanoparticles and/or nanoparticle compositions. A substance or agent to be delivered in conjunction with nanoparticles and/or nanoparticle compositions may or may not be attached to the AE nanoparticles and/or nanoparticle compositions by adsorption forces.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than 90%, 91%, 92%, 93%, 94%, 95%, 96%, 97%, 98%, 99% pure.

Microfluidized: As used herein, the term "microfluidized" means exposed to high shear forces. In some embodiments, such exposure to high shear forces is accomplished by exposure to high pressure; in some embodiments such high pressure is within the range of about 15,000 to about 26,000 psi. In some embodiments, such exposure to high shear forces is accomplished by cavitation. In some embodiments, such exposure to high shear forces is accomplished by passing a sample through an instrument such as, for example, a Microfluidizer® (Microfluidics Corporation/MFIC Corporation) or other like device that may be useful in creating a uniform nanoparticle composition. In some embodiments of the present invention, a sample is microfluidized through exposure to high shear forces for a period of time less than about 10 minutes. In some embodiments, the period of time is less than about 9, 8, 7, 6, 5, 4, 3, 2, or 1 minute(s). In some embodiments, the period of time is within the range of about 1-2 minutes. In some embodiments, the period of time is less than 1 minute. In some embodiments, the period of time is about 30 seconds. In some embodiments of the invention, a sample is "microfluidized" through a single exposure to high shear forces; such embodiments are referred to as "single pass" microfluidization.

Nanoparticle: As used herein, the term "nanoparticle" refers to any particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane. A "micellar membrane" comprises amphiphilic entities which have aggregated to surround and enclose a space or compartment (e.g., to define a lumen).

Nanoparticle composition: As used herein, the term "nanoparticle composition" refers to any substance that contains at least one AE nanoparticle. In some embodiments, a nanoparticle composition is a uniform collection of AE nanoparticles. In some embodiments, nanoparticle compositions are dispersions or emulsions. In general, a dispersion or emulsion is formed when at least two immiscible materials are combined. An "oil-in-water" dispersion is one in which oily particles (or hydrophobic or non-polar) are dispersed within an aqueous dispersion medium. A "water-in-oil" dispersion is one in which aqueous (or hydrophilic or polar) particles are dispersed within an oily dispersion medium. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories. In some embodiments, nanoparticle compositions are nanoemulsions. In some embodiments, nanoparticle compositions comprise micelles. In some embodiments, a nanoparticle composition is stable. In some embodiments, a nanoparticle composition includes one or more biologically active agents to be delivered in conjunction with the AE nanoparticles.

Not contaminated with: The phrase "not contaminated with," when used herein to refer to a nanoparticle composition, is synonymous with "substantially free of" and describes a nanoparticle composition containing no more than about 50% of the recited material. For example, if a nanoparticle composition is said to be "substantially free of" particles whose diameter is outside of a stated range, then no more than about 50% of the particles in that composition have diameters outside of the range. In some embodiments, no more than 25% of the particles are outside of the range. In some embodiments, no more than 20%, 19%, 18%, 17%, 16%, 15%, 14%, 13%, 12%, 10%, 9%, 8%, 7%, 6%, 5%, 4%, 3%, 2%, 1%, 0.5% or less of the particles have diameters outside of the stated range.

Nucleic acid: As used herein, the term "nucleic acid," in its broadest sense, refers to any compound and/or substance that can be incorporated into an oligonucleotide chain. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns.

Nutraceutical: As used herein, the term "nutraceutical" refers to any substance thought to provide medical, health, or biological benefits. In some embodiments, nutraceuticals may prevent disease. In some embodiments, nutraceuticals may provide basic nutritional value. In some embodiments, a nutraceutical is a food or part of a food. In some embodiments, a nutraceutical agent may be a class of isolated nutrients, dietary supplements, vitamins, minerals, herbs, fortified foods, healing foods, genetically engineered foods, and processed foods. Nutraceuticals may also be known as "phytochemical foods" or "functional foods."

Patient: A "patient," or "subject," as used herein, means an animal. In some embodiments, the animal is a mammal, commonly a human.

Premix: As used herein, the term "premix" refers to any combination of components that is subsequently used to generate a nanoparticle composition according to the present invention. For example, a premix is any collection of ingredients that, when subject to high shear forces, generates AE nanoparticles according to the present invention. In some embodiments, a premix contains two or more immiscible solvents. In some embodiments, a premix contains components that self-assemble into microparticles or nanoparticles. In some embodiments, a premix contains components that self-assemble into micelles. In some embodiments, a premix contains one or more peptides as described in PCT application serial number PCT/US07/086040 entitled "Peptide Nanoparticles and Uses Therefor," filed Nov. 30, 2007. In some embodiments, a premix contains one or more unmodified peptides; in some embodiments, a premix contains at least one other biologically active agent. In some embodiments, a premix is agitated, mixed and/or stirred; in some embodiments, a premix is agitated, mixed, and/or stirred prior to being subjected to high shear force. In some embodiments, a premix comprises at least one solubilized component (i.e., at least one component that is in solution); in some such embodiments, the premix is subject to high shear force after such solubilization is achieved.

Pure: As used herein, a substance and/or entity is "pure" if it is substantially free of other components. For example, a preparation that contains more than about 90% of a particular substance and/or entity is typically considered to be a pure preparation. In some embodiments, a substance and/or entity is at least 91%, 92%, 93%, 94%, 95%, 96%, 97%, 98%, or 99% pure.

Shear force: As used herein, the term "shear force" refers to a force that is parallel to the face of a material, as opposed to a force that is perpendicular to the face of a material. In some embodiments, a composition exposed to high shear forces in order to produce a uniform nanoparticle composition. Any method known in the art can be used to generate high shear forces. In some embodiments, cavitation is used to generate high shear forces. In some embodiments, high pressure homogenization is used to generate high shear forces. Alternatively or additionally, high shear force may be administered by exposure to high pressure, for example about 15,000 psi. In some embodiments, such high pressure is within the range of about 18,000 to about 26,000 psi; in some embodiments, it is within the range of about 20,000 to about 25,000 psi. In some embodiments, a Microfluidizer® Processor (Microfluidics Corporation/MFIC Corporation) or other like device is used to generate high shear force. Microfluidizer® Processors provide high pressure and a resultant high shear rate by accelerating a composition through microchannels (typically having dimensions on the order of 75 microns) at a high velocity (typically in the range of 50 m/s to 300 m/s) for size reduction to the nanoscale range. As the fluid exits the microchannels it forms jets which collide with jets from opposing microchannels. In the channels the fluid experiences high shear (up to $10^7$ 1/s) which is orders of magnitude higher than that of conventional technologies. Jet collisions result in mixing in submicron level. Therefore, in such devices, high shear and/or impact can achieve particle size reduction and mixing of multiphase. In some embodiments of the present invention, a sample is exposed to high shear forces for a period of time less than about 10 minutes. In some embodiments, the period of time is less than about 9, about 8, about 7, about 6, about 5, about 4, about 3, about 2, or about 1 minute(s). In some embodiments, the period of time is within the range of about 1 to about 2 minutes or less; in some embodiments, the period of time is about 30 seconds. In some embodiments of the invention, a sample is "microfluidized" through a single exposure to high shear forces; such embodiments are referred to herein as "single pass" microfluidization.

Small Molecule: In general, a "small molecule" is understood in the art to be an organic molecule that is less than about 5 kilodaltons (Kd) in size. In some embodiments, the small molecule is less than about 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Subject: As used herein, the term "subject" or "patient" refers to any organism to which a composition of this invention may be administered, e.g., for experimental, diagnostic, prophylactic, and/or therapeutic purposes. Typical subjects include animals (e.g., mammals such as mice, rats, rabbits, non-human primates, and humans; insects; worms; etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Stable: The term "stable," when applied to nanoparticle compositions herein, means that the compositions maintain one or more aspects of their physical structure (e.g., size range and/or distribution of particles) over a period of time. In some embodiments of the invention, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time. In some embodiments, the period of time is at least about one hour; in some embodiments the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, or longer. In some embodiments, the period of time is within the range of about one (1) day to about twenty-four (24) months, about two (2) weeks to about twelve (12) months, about two (2) months to about five (5) months, etc. For example, if a nanoparticle composition is subjected to prolonged storage, temperature changes, and/or pH changes and a majority of the nanoparticles in the population maintain a diameter within a stated range (i.e., for example, between approximately 10 nm-120 nm), the nanoparticle composition is stable. For some such populations, a majority is more than about 50%, about 60%, about 70%, about 80%, about 90%, about 95%, about 96%, about 97%, about 98%, about 99%, about 99.5%, about 99.6%, about 99.7%, about 99.8%, about 99.9%, or more. In some embodiments of the invention, where a nanoparticle composition comprises one or more biologically active agents (e.g. botulinum toxin), the nanoparticle composition is considered stable if the concentration of biologically active agent is maintained in the composition over the designated period of time under a designated set of conditions.

Substantially free of: An inventive nanoparticle composition is said to be "substantially free of" particles whose diameter is outside of a stated range when no more than about 50% of the particles in that composition have diameters outside of the range. In some embodiments, no more than 25% of the particles are outside of the range. In some embodiments, no more than 20%, 19%, 18%, 17%, 16%, 15%, 14%, 13%, 12%, 10%, 9%, 8%, 7%, 6%, 5%, 4%, 3%, 2%, 1%, 0.5% or less of the particles have diameters outside of the stated range.

Suffering from: An individual who is "suffering from" a disease, disorder, or condition (e.g., facial wrinkles) has been diagnosed with or exhibits symptoms of the disease, disorder, or condition.

Therapeutically effective amount: As used herein, the term "therapeutically effective amount" means an amount of inventive AE nanoparticle composition that is sufficient, when administered to a patient suffering from or susceptible to a disease, disorder, and/or condition, to treat the disease, disorder, and/or condition.

Therapeutic agent: As used herein, the phrase "therapeutic agent" refers to any agent that, when administered to a subject, has a therapeutic effect and/or elicits a desired biological and/or pharmacological effect.

Toxic solvent: As used herein, the term "toxic solvent" refers to any substance that may alter, disrupt, remove, or destroy an animal's tissue. As would be understood by one of ordinary skill in the art, an animal's tissue can include living cells, dead cells, extracellular matrix, cellular junctions, biological molecules, etc. To give but a few examples, toxic solvents include dimethyl sulfoxide, dimethyl acetimide, dimethyl foramide, chloroform, tetramethyl foramide, acetone, acetates, and alkanes.

Treatment: As used herein, the term "treatment" (also "treat" or "treating") refers to any administration of a biologically active agent that partially or completely alleviates, ameliorates, relives, inhibits, delays onset of, reduces severity of, and/or reduces incidence of one or more symptoms or features of a particular disease, disorder, and/or condition (e.g., facial wrinkles). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Uniform: The term "uniform," when used herein in reference to a nanoparticle composition, refers to a nanoparticle composition in which the individual nanoparticles have a specified range of particle diameter sizes. For example, in some embodiments, a uniform nanoparticle composition is one in which the difference between the minimum diameter and maximum diameter does not exceed approximately 600, approximately 550, approximately 500, approximately 450, approximately 400, approximately 350, approximately 300, approximately 250, approximately 200, approximately 150, approximately 100, approximately 90, approximately 80, approximately 70, approximately 60, approximately 50, or fewer nm. In some embodiments, particles (e.g., AE nanoparticles) within inventive uniform nanoparticle compositions have diameters that are smaller than about 600, about 550, about 500, about 450, about 400, about 350, about 300, about 250, about 200, about 150, about 130, about 120, about 115, about 110, about 100, about 90, about 80 nm, or less. In some embodiments, particles (e.g., AE nanoparticles) within inventive uniform nanoparticle compositions have diameters within the range of about 10 and about 600 nanometers. In some embodiments, particles (e.g., AE nanoparticles) within inventive uniform nanoparticle compositions have diameters within the range of about 10 to about 300, about 10 to about 200, about 10 to about 150, about 10 to about 130, about 10 to about 120, about 10 to about 115, about 10 to about 110, about 10 to about 100, or about 10 to about 90 nm. In some embodiments, particles (e.g., AE nanoparticles) within inventive botulinum nanoparticle compositions have an average particle size that is under about 300, about 250, about 200, about 150, about 130, about 120, about 115, about 110, about 100, or about 90 nm. In some embodiments, the average particle size is within the range of about about 10 to about 300, about 50 to about 250, about 60 to about 200, about 65 to about 150, about 70 to about 130 nm. In some embodiments, the average particle size is about 80 to about 110 nm. In some embodiments, the average particle size is about 90 to about 100 nm. In some embodiments, a majority of the particles (e.g., AE nanoparticles) within inventive uniform nanoparticle compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition. In some embodiments of the invention, a uniform nanoparticle composition is achieved by microfluidization of a sample. In some embodiments of the invention, a uniform nanoparticle composition is prepared by exposure to high shear force, e.g., by microfluidization.

Vector: As used herein, "vector" refers to a nucleic acid molecule which can transport another nucleic acid to which it has been linked. In some embodiment, vectors can achieve extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DESCRIPTION OF CERTAIN PREFERRED EMBODIMENTS

Amphiphilic Entity (AE) Nanoparticles

In some embodiments, the present invention provides compositions containing AE nanoparticles. In some embodiments, the nanoparticle compositions are stable (i.e. the particles of the nanoparticle composition stay within a stated range over time and when subjected to temperature and/or pH changes). In some embodiments, the nanoparticle compositions are sterile (i.e. the nanoparticle composition contains no living cellular contaminants) In some embodiments, the nanoparticle compositions are bacteria-resistant (i.e. the nanoparticle compositions are characterized by no observable bacterial growth). In some embodiments, the nanoparticle compositions comprising AE nanoparticles are completely free or substantially free of toxic components. In some embodiments, the AE nanoparticles are completely free or substantially free of toxic components.

In some embodiments, the nanoparticle compositions are uniform. In some embodiments, a uniform nanoparticle composition comprises a population of particles whose difference between the minimum and maximum diameters does not exceed approximately 600 nm, approximately 550 nm, approximately 500 nm, approximately 450 nm, approximately 400 nm, approximately 350 nm, approximately 300 nm, approximately 250 nm, approximately 200 nm, approximately 150 nm, or approximately 100 nm.

In some embodiments, AE nanoparticles inventive nanoparticle compositions have diameters that are smaller than about 1000, about 600, about 550, about 500, about 450, about 400, about 350, about 300, about 250, about 200, about 150, about 130, about 120, about 115, about 110, about 100, about 90, about 80, about 50 nm, or less.

In some embodiments, inventive AE nanoparticles have a diameter of 1 to 1000 nm, 1 to 600 nm, 1 to 500 nm, 1 to 400 nm, 1 to 300 nm, 1 to 200 nm, 1 to 150 nm, 1 to 120 nm, 1 to 100 nm, 1 to 75 nm, 1 to 50 nm, or 1 to 25 nm. In some embodiments, inventive AE nanoparticles have a diameter of 1 to 15 nm, 15 to 200 nm, 25 to 200 nm, 50 to 200 nm, or 75 to 200 nm.

In some embodiments, the total particle distribution is encompassed within the specified range of particle diameter size. In some embodiments, less than 50%, 25%, 10%, 5%, or 1% of the total particle distribution is outside of the specified range of particle diameter sizes. In some embodiments, less than 1% of the total particle distribution is outside of the specified range of particle diameter sizes. In certain embodiments, the nanoparticle composition is substantially free of particles having a diameter larger than 300 nm, 250 nm, 200 nm, 150 nm, 120 nm, 100 nm, 75 nm, 50 nm, or 25 nm.

In some embodiments, AE nanoparticles within inventive nanoparticle compositions have an average particle size that is under about 300, about 250, about 200, about 150, about 130, about 120, about 115, about 110, about 100, about 90, or about 50 nm. In some embodiments, the average particle size is within the range of about 10 to about 300, about 50 to about 250, about 60 to about 200, about 65 to about 150, about 70 to about 130 nm. In some embodiments, the average particle size is about 80 to about 110 nm. In some embodiments, the average particle size is about 90 to about 100 nm.

In some embodiments, inventive nanoparticle compositions are substantially free of particles having a diameter in excess of 300 nm. Specifically, in some embodiments, fewer than 50%, of the nanoparticles in inventive nanoparticle compositions have a diameter in excess of 300 nm. In some embodiments, fewer than 25% of the particles have a diameter in excess of 300 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 300 nm. Furthermore, in some embodiments, the nanoparticles in inventive nanoparticle compositions have diameters within the range of 10 to 300 nm.

In some embodiments, inventive nanoparticle compositions are substantially free of particles having a diameter in excess of 200 nm. Specifically, in some embodiments, fewer than 50%, of the nanoparticles in inventive nanoparticle compositions have a diameter in excess of 200 nm. In some embodiments, fewer than 25% of the particles have a diameter in excess of 200 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 200 nm. Furthermore, in some embodiments, the nanoparticles in inventive nanoparticle compositions have diameters within the range of 10 to 200 nm.

In some embodiments, inventive nanoparticle compositions are substantially free of particles having a diameter in excess of 120 nm. Specifically, in some embodiments, fewer than 50%, of the nanoparticles in inventive nanoparticle compositions have a diameter in excess of 120 nm. In some embodiments, fewer than 25% of the particles have a diameter in excess of 120 nm. In some embodiments, fewer than 20%, 19%, 18%, 17%, 16%, 15%, 14%, 13%, 12%, 10%, 9%, 8%, 7%, 6%, 5%, 4%, 3%, 2%, 1%, 0.5% or less of the particles have a diameter in excess of 120 nm. Furthermore, in some embodiments, the nanoparticles in inventive nanoparticle compositions have diameters within the range of 10 to 120 nm.

In some embodiments, a majority of the AE nanoparticles within inventive compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition.

Zeta potential is a measurement of the electric potential at a shear plane. A shear plane is an imaginary surface separating a thin layer of liquid bound to a solid surface (e.g. the surface of inventive nanoparticles) and showing elastic behavior from the rest of liquid (e.g. liquid dispersion medium) showing normal viscous behavior. In some embodiments, inventive AE nanoparticles have a zeta potential ranging between −50 mV to +50 mV. In some embodiments, inventive AE nanoparticles have a zeta potential ranging between −25 mV to +25 mV. In some embodiments, inventive AE nanoparticles have a zeta potential ranging between −10 mV to +10 mV.

In some embodiments, the AE nanoparticles are micelles. In some embodiments, the AE nanoparticles provided in accordance with the present invention are nanospheres. In some embodiments, the AE nanoparticles comprise one or more amphiphilic entities. Inventive AE nanoparticles may optionally comprise one or more dispersion media, surfactants, biologically active agents, or release-retarding ingredients.

Inventive nanoparticle compositions may be emulsions or dispersions. In some embodiments, the compositions are "oil-in-water" dispersions (i.e., dispersions in which oily particles are dispersed within an aqueous dispersion medium); in some embodiments, the compositions are "water-in-oil" dispersions (i.e., dispersions in which aqueous particles are dispersed within an oily dispersion medium). In some embodiments, some or all of the nanoparticles have a micellar structure in which a lumen is enclosed by a micellar "membrane." In some such embodiments, the lumen of the micelle has the same character (e.g., aqueous vs. oily) as the dispersion medium and the micellar membrane has the opposing character (e.g., oily vs. aqueous); in some embodiments, the lumen of the micelle has the same character as the micellar membrane and the dispersion medium has the opposing character.

Premix

In some embodiments, the invention provides methods of preparing the inventive AE nanoparticles. The method generally involves combining one or more amphiphilic entities to form a "premix" and applying high shear forces to the premix. The premix generally contains one or more amphiphilic entities and one or more dispersion media. In some embodiments, the premix may also contain one or more additional substances such as, for example, surfactants, biologically active agents, release-retarding ingredients, etc. Those of ordinary skill in the art, however, will appreciate that it is not essential that all components necessarily be present in the premix (or be present in their total eventual amount) in the premix; in some instances it may be desirable or appropriate to add or to supplement one or more components later.

In some embodiments, the premix components are selected and/or maintained under conditions that permit nanoparticle formation before the high shear forces are applied. In some embodiments, the premix is not maintained under conditions that permit particle formation before the high shear forces are applied. In some embodiments, these particles are nano- or micro-particles. In some embodiments, these particles are micelles. In some embodiments, nanoparticles are allowed to form from the premix components before the high shear forces are applied. In some embodiments, nanoparticle formation in the premix is inhibited before the high shear forces are applied. In certain embodiments, the high shear forces are applied after nanoparticles have formed from the premix components. In certain embodiments, the high shear forces are applied before nanoparticles form from the premix components. In certain embodiments, the high shear forces are applied while nanoparticles are forming from the premix components.

In some embodiments, the present invention provides methods of manufacturing AE nanoparticles. The method generally involves preparing a premix of two or more amphiphilic entities and subjecting the premix to high shear forces. In some embodiments, the premix may comprise one or more dispersion media, surfactants, biologically active agents, or release-retarding ingredients.

In some embodiments, the methods of producing inventive AE nanoparticles involve steps of providing a premix, allowing or inducing assembly of particles (e.g., nanoparticles, microparticles, and/or micelles) within the premix, and subjecting the particles to high shear forces such that an inventive nanoparticle composition is obtained. In some embodiments, particle formation in the premix may be by emulsion polymerization, self-assembly, or by any other known technique for producing micro- or nano-particles.

In certain embodiments, particle formation in the premix may involve the steps of dissolving an amphiphilic entity in a dispersion medium, gradually adding water to the solution of dispersion medium and amphiphilic entity, and waiting for particles (e.g. nanoparticles, microparticles, and/or micelles) to self-assemble. In some embodiments, particle formation can be induced by slowly cooling the solution.

In certain embodiments, particle formation in the premix may involve the steps of dissolving an amphiphilic entity in a dispersion medium such as water, stirring for 5, 6, 7, 8, 9, 10, 11, 12, 13, 14, or 15 hours while allowing particles (e.g. nanoparticles, microparticles, and/or micelles) to form, dialyzing against water to remove any organic dispersion medium to stabilize the particles, and freeze-drying to produce a composition.

In some embodiments of the present invention that utilize a premix, it is to be understood that the premix components may assemble into particles before the application of high shear force. At least some of such particles may be microparticles or even nanoparticles. In some embodiments, an inventive nanoparticle composition is prepared from a premix, wherein the premix is selected from the group comprising a suspension or a microemulsion. In some embodiments, however, particle structures do not form in the premix before application of high shear force.

In some embodiments of the present invention, all of the components present in the final nanoparticle composition are present in the premix and are subjected to high shear force to produce the nanoparticle composition. In some embodiments of the present invention, one or more of the components that are present in the final nanoparticle composition is/are missing from the premix or is/are present in the premix in a smaller amount than in the final nanoparticle composition. That is, in some embodiments of the present invention, one or more materials are added to the nanoparticle composition after the premix is subjected to high shear stress.

In certain embodiments of the invention, the premix is prepared as a solution prior to application of high shear force. In particular, for nanoparticle compositions that include at least one biologically active agent (e.g., an unmodified peptide), it is often desirable for the biologically active agent to be dissolved in the premix before the high shear stress is applied. Thus, in many embodiments, the biologically active agent is soluble in at least one of the media (or in a combination of media utilized in the premix). In some embodiments of the invention, such dissolution requires heating; in other embodiments it does not.

Below, we discuss exemplary components of a premix that is subjected to high shear force according to the present invention.

Amphiphilic Entities

The present invention provides nanoparticles and nanoparticle compositions comprising amphiphilic entities. Useful amphiphilic entities include natural entities, synthetic entities, and entities that contain both natural and synthetic components. In some embodiments, amphiphilic entities may comprise one or more polymers, and/or one or more compounds with polymeric character.

As discussed above, an amphiphilic entity is one that has both hydrophobic and hydrophilic natures. As will be appreciated by those of ordinary skill in the art, an amphiphilic entity can be comprised in any number of different ways. In some embodiments, an amphiphilic entity may comprise one or more individual compounds or substances that is itself amphiphilic. To give but a few examples, such compounds or molecules include polyethylene glycol (PEG), phospholipids, cholesterols, glycolipids fatty acids, bile acids, and saponins. PEG is generally recognized as safe for use in food, cosmetics, and medicines by the US Food and Drug Administration. PEG is water-soluble, non-toxic, odorless, lubricating, nonvolatile, and nonirritating.

In some embodiments, an amphiphilic entity may comprise one or more individual components that is not itself amphiphilic but that has some hydrophilic or hydrophobic character. In such embodiments, two or more such non-amphiphilic components will typically be associated with one another such that the assemblage of the individual components is amphiphilic. Such association may or may not involve covalent linkage; such association may involve non-covalent bonding (e.g., via electrostatic interactions, affinity interactions, hydrophobic interactions, hydrogen bonding, Van der Waals interactions, ionic interaction, dipole-dipole interaction, etc.). In general, such association may involve any relevant force, bond, or means of adhesion.

In some embodiments, an amphiphilic entity of the present invention may be constructed from two or more individual components having differing degrees of hydrophilicity or hydrophobicity. In certain embodiments, an amphiphilic entity may comprise at least one hydrophilic component and at least one hydrophobic component. In certain embodiments, the "hydrophilic" and "hydrophobic" components are either hydrophilic or hydrophobic relative to one another.

In some embodiments, two or more components of differing degrees of hydrophilicity or hydrophobicity may be bonded together by covalent bonds to form a homopolymer or a co-polymer. In some embodiments, a co-polymer may be a block co-polymer. In some embodiments, a co-polymer may be a graft co-polymer.

In some embodiments, an amphiphilic entity may comprise or consist of an amphiphilic block co-polymer. In some embodiments, an amphiphilic block co-polymer may be a diblock co-polymer. In certain embodiments, an amphiphilic diblock co-polymer may comprise a first polymer block and a second polymer block connected covalently at the chain ends. In specific embodiments, the first polymer block may comprise repeating units of a hydrophilic component, and the second polymer block may comprise repeating units of a hydrophobic component. In specific embodiments, the first polymer block may comprise repeating units of a hydrophobic component, and the second polymer block may comprise repeating units of a hydrophilic component. In some embodiments, an amphiphilic block co-polymer may be a multiblock co-polymer. In certain embodiments, an amphiphilic block co-polymer may comprise multiple alternating blocks of two or more polymers connected covalently at the chain ends. In specific embodiments, an amphiphilic block co-polymer may comprise multiple alternating hydrophilic blocks and hydrophobic blocks connected covalently at the chain ends. In specific embodiments, each block of the alternating blocks may comprise repeating units of either hydrophilic components or hydrophobic components.

In some embodiments, an amphiphilic entity may comprise or consist of an amphiphilic graft co-polymer. In some embodiments, an amphiphilic graft co-polymer may comprise or consist of blocks of polymers connected covalently to the side chains of other blocks of polymers. In specific embodiments, each polymer block may comprise or consist of repeating units of either hydrophilic or hydrophobic components. In certain embodiments, an amphiphilic graft co-polymer may comprise or consist of a first polymer block and a second polymer block connected covalently to a side chain of the first polymer block. In certain embodiments, the first polymer block may comprise or consist of repeating units of a hydrophilic component, and the second block may comprise repeating units of a hydrophobic component. In certain embodiments, the first polymer block may comprise or consist of repeating units of a hydrophobic component, and the second block may comprise repeating units of a hydrophilic component.

In some embodiments, an amphiphilic block or graft co-polymer may include a hydrophilic polymer block comprising repeating units of a polysaccharide and a hydrophobic polymer block comprising repeating units of a polyester or polysaccharide. Alternatively or additionally, an amphiphilic block or graft co-polymer may include a hydrophobic polymer block comprising repeating units of a polysaccharide and a hydrophilic polymer block comprising repeating units of a polyester or polysaccharide. Such a hydrophilic polymer block can contain repeating units of any type of hydrophilic polymer, such as a polysaccharide (e.g. pullulan) or polyalkene oxide (e.g. polyethylene oxide). The hydrophobic polymer block can contain repeating units of any type of hydrophobic polymer, such as a polycaprolactone, poly (lactic acid), poly (glycolic acid), poly dioxanone, copolymers of these or polyamide (e.g. polycaprolactam).

In some embodiments, the hydrophilic portion of the amphiphilic entity may be non-ionic. In some embodiments, the hydrophilic component of an amphiphilic entity comprises one or more ionic groups. In general, such ionic groups are hydrophilic and can confer hydrophilic nature on the amphiphilic entity.

In some embodiments, the ionic group may be cationic. In some embodiments, the cationic group may be an ammonium ($NH_4^+$), nitronium ($NO_2^+$), nitrosyl ($NO^+$), hydronium ($H_3O^+$), mercurous ($Hg_2^{2+}$), phosphonium ($PH_4^+$), vanadyl ($VO^{2+}$), or salt thereof.

In some embodiments, the ionic group may be anionic. In some embodiments, the anionic group may be a fatty acid, arsenide ($As^{3-}$), azide ($N_3^-$), bromide ($Br^-$), chloride ($Cl^-$), fluoride ($F^-$), hydride ($H^-$), iodide ($I^-$), nitride ($N^{3-}$), oxide ($O^{2-}$), phosphide ($P^{3-}$), selenide ($Se^{2-}$), sulfide ($S^{2-}$), peroxide ($O_2^{2-}$), arsenate ($AsO_4^{3-}$), arsenite ($AsO_3^{3-}$), borate ($BO_3^{3-}$), perbromate ($BrO_4^-$), bromate ($BrO_3^-$), bromite ($BrO_2^-$), hypobromite ($BrO^-$), carbonate ($CO_3^{2-}$), hydrogen carbonate ($HCO_3^-$), chlorate ($ClO_3^-$), perchlorate ($ClO_4^-$), chlorite ($ClO_2^-$), hypochlorite ($ClO^-$), chromate ($CrO_4^{2-}$), dichromate ($Cr_2O_7^{2-}$), perfluorate ($BrO_4^-$), fluorate ($BrO_3^-$), fluorite ($BrO_2^-$), hypofluorite ($BrO^-$), periodate ($IO_4^-$), iodate ($IO_3^-$), iodite ($IO_2^-$), hypoiodite ($IO^-$), nitrate ($NO_3^-$), nitrite ($NO_2^-$), phosphate ($PO_4^{3-}$), hydrogen phosphate ($HPO_4^{2-}$), dihydrogen phosphate ($H_2PO_4^-$), phosphite ($PO_3^{3-}$), silicate ($SiO_3^{2-}$), sulfate ($SO_4^{2-}$), thiosulfate ($S_2O_3^{2-}$), hydrogen sulfate ($HSO_4^-$), sulfite ($SO_3^{2-}$), hydrogen sulfite ($HSO_3^-$), sulfonate ($—S(=O)_2—O^-$), acetate ($C_2H_3O_2^-$), formate ($HCO_2^-$), oxalate ($C_2O_4^{2-}$), hydrogen oxalate ($HC_2O_4^-$), citrate ($C_6H_5O_7^{3-}$), succinate ($C_4H_4O_4^{2-}$), fumarate ($C_4H_2O_4^{2-}$), malate ($C_4H_5O_5^{2-}$), hydrogen sulfide ($HS^-$), telluride ($Te^{2-}$), amide ($NH_2^-$), cyanate ($OCN^-$), thiocyanate ($SCN^-$), cyanide ($CN^-$), hydroxide ($OH^-$), permanganate ($MnO_4^-$), or salt thereof.

In some embodiments, the hydrophilic component of an amphiphilic entity may comprise or consist of a nucleic acid. For example, the nucleic acid polymer may include DNA, RNA, or combinations thereof. In some embodiments, the nucleic acid polymer may be an oligonucleotide and/or polynucleotide. In some embodiments, the nucleic acid polymer may be an oligonucleotide and/or modified oligonucleotide; an antisense oligonucleotide and/or modified antisense oligonucleotide; a cDNA; a genomic DNA; viral DNA and/or RNA; DNA and/or RNA chimeras; plasmids; cosmids; gene fragments; an artificial and/or natural chromosome (e.g. a yeast artificial chromosome) and/or a part thereof; an RNA (e.g. an mRNA, a tRNA, an rRNA and/or a ribozyme); a peptide nucleic acid (PNA); a polynucleotide comprising synthetic analogues of nucleic acids, which may be modified or unmodified; various structural forms of DNA including single-stranded DNA, double-stranded DNA, supercoiled DNA and/or triple-helical DNA; Z-DNA; and/or combinations thereof.

In some embodiments, the hydrophilic component of an amphiphilic entity may comprise or consist of a carbohydrate. In some embodiments, the carbohydrate may be a polysaccharide composed of simple sugars (or their derivatives) connected by glycosidic bonds, as known in the art. Such sugars may include, but are not limited to, glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In some embodiments, the polymer may be a hydrophilic carbohydrate, including aminated, carboxylated, and sulfated polysaccharides. In some embodiments, the hydrophilic carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan. In some embodiments, hydrophilic polysaccharides can be modified to become hydrophobic by introducing a large number of side-chain hydrophobic groups. In some embodiments, a hydrophobic carbohydrate may include cellulose acetate, pullulan acetate, konjac acetate, amylose acetate, and dextran acetate.

In some embodiments, the hydrophilic component of an amphiphilic entity may comprise or consist of a gum including, but not limited to, xanthan gum, alginic acid, caraya gum, sodium alginate, and/or locust bean gum.

In some embodiments, a component of an amphiphilic entity may comprise or consist of a protein. In some embodiments, a protein is a hydrophilic component of an amphiphilic entity. In other embodiments, a protein is a hydrophobic component of an amphiphilic entity. Exemplary proteins that may be used in accordance with the present invention include, but are not limited to, albumin, collagen, or a poly(amino acid) (e.g. polylysine).

In some embodiments, the hydrophobic component of an amphiphilic entity may comprise or consist of one or more fatty acid groups or salts thereof. In general, such groups are typically hydrophobic and can confer hydrophobic nature onto the amphiphilic entity. In some embodiments, the fatty acid group may comprise digestible, long chain (e.g., $C_8$-$C_{50}$), substituted or unsubstituted hydrocarbons. In some embodiments, the fatty acid group may be a $C_{10}$-$C_{20}$ fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, the hydrophobic component of an amphiphilic entity may comprise or consist of one or more biocompatible and/or biodegradable synthetic polymers, including, for example, polyethylenes, polycarbonates (e.g. poly(1,3-dioxan-2one)), polyanhydrides (e.g. poly(sebacic anhydride)), polyhydroxyacids (e.g. poly(β-hydroxyalkanoate)), polypropylfumerates, polycaprolactones, polyamides (e.g. polycaprolactam), polyacetals, polyethers, polyesters (e.g. polylactide and polyglycolide), biodegradable polycyanoacrylates, polyvinyl alcohols, and biodegradable polyurethanes. For example, the amphiphilic entity may comprise one or more of the following biodegradable polymers: poly(lactic acid), poly(glycolic acid), poly(caprolactone), poly(lactide-co-glycolide), poly(lactide-co-caprolactone), poly(glycolide-co-caprolactone), and poly(DL-lactide-co-glycolide).

In some embodiments, the hydrophobic component of an amphiphilic entity may comprise or consist of one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers. The acrylic polymer may comprise fully-polymerized copolymers of acrylic and methacrylic acid esters with a low content of quaternary ammonium groups.

In some embodiments, the hydrophobic component of an amphiphilic entity may comprise or consist of a polyester. Exemplary such polyesters include, for example, polyalkylene glycols, poly(glycolide-co-lactide), PEGylated poly(lactic-co-glycolic acid), poly(lactic acid), PEGylated poly(lactic acid), poly(glycolic acid), PEGylated poly(glycolic acid), co-polymers of polylactic and polyglycolic acid, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), and derivatives thereof. In some embodiments, polyesters may include, for example, polycaprolactone, poly(L-lactide-co-L-lysine), poly(serine ester), poly(4-hydroxy-L-proline ester), poly[α-(4-aminobutyl)-L-glycolic acid], and derivatives thereof.

In some embodiments, amphiphilic entities may have biological activity.

Those skilled in the art will recognize that this is an exemplary, not comprehensive, list of amphiphilic entities. The percent of amphiphilic entity in the composition from which AE nanoparticles are prepared (e.g., in the premix) can range from 40% to 99%, from 50% to 99%, from 60% to 99%, from 70% to 99%, from 80% to 99%, from 80% to 90%, or from 90% to 99%. In some embodiments the percent of amphiphilic entity in the composition from which AE nanoparticles are prepared (e.g., in the premix) is approximately 75%, approximately 76%, approximately 77%, approximately 78%, approximately 79%, approximately 80%, approximately 81%, approximately 82%, approximately 83%, approximately 84%, approximately 85%, approximately 86%, approximately 87%, approximately 88%, approximately 89%, approximately 90%, approximately 91%, approximately 92%, approximately 93%, approximately 94%, approximately 95%, approximately 96%, approximately 97%, approximately 98%, or approximately 99%.

Dispersion Media

In general, the premix is expected to contain at least one dispersion medium. In some embodiments, the premix may contain a hydrophilic dispersion medium. In some embodiments, the premix may contain a hydrophobic dispersion medium. In some embodiments, the premix may contain a combination of two or more dispersion media, for example of different characters. In some embodiments, the premix may contain at least two immiscible dispersion media.

It will be appreciated that the selection of appropriate dispersion medium will depend, at least in part, on the nature of the amphiphilic entit(ies) being employed and on whether it is intended for the intended external and internal character of the intended nanoparticles. For example, in some embodiments, the nanoparticles will have hydrophilic external character and hydrophobic internal character; in some embodiments, the nanoparticles will have hydrophobic external character and hydrophilic character; in some embodiments, the nanoparticles will have hydrophilic external and internal character; and in some embodiments, the nanoparticles with have hydrophobic external and internal character. It will be appreciated by those of ordinary skill in the art that the same nanoparticle components can sometimes assemble into different nanoparticle structures, having different internal and external characters. To give but one example, nanoparticles formed from a monolayer of an individual amphiphilic compound will have differing external and internal characters, whereas nanoparticles formed from a bilayer of the same compound will have the same external and internal character.

In some embodiments of the invention, hydrophilic dispersion media are utilized. In some embodiments, such hydrophilic dispersion media are aqueous. Such aqueous dispersion media include but are not limited to, water, short chain alcohols (e.g. ethanol), oils, 5% dextrose, Ringer's solutions (e.g. lactated Ringer's injection, lactated Ringer's plus 5% dextrose injection, aceylated Ringer's injection), Normosol-M, Isolyte E, dimethyl sulfoxide (DMSO), dimethyl acetamide, dimethyl formamide, chloroform, tetramethyl formamide, carbon tetrachloride, N-methyl pyrolidone, or dichloroethane, and the like, and combinations thereof.

In some embodiments of the invention, hydrophobic dispersion media are utilized. In some embodiments, such hydrophobic dispersion media are oils. In general, any oil known in the art is suitable for use in making the inventive AE nanoparticles. In some embodiments, the oil may comprise one or more fatty acid groups or salts thereof. In some embodiments, the fatty acid group may comprise digestible, long chain (e.g., $C_8$-$C_{50}$), substituted or unsubstituted hydrocarbons. In some embodiments, the fatty acid group may be a $C_{10}$-$C_{20}$ fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In some embodiments, the oil is a liquid triglyceride. In certain embodiments, the oil is a medium chain (e.g., 6-12 carbons) triglyceride (e.g., Labrafac WL 1349, coconut oil, palm kernel oil, camphor tree drupe oil, etc.). In certain embodiments, the oil is a short chain (e.g., 2-5 carbons) triglyceride. In certain embodiments, the oil is a long chain (e.g., greater than 12 carbons) triglyceride (e.g., soybean oil, sunflower oil, etc.).

Suitable oils for use with the present invention include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, and combinations thereof. Suitable oils for use with the present invention include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Those of ordinary skill in the art will appreciate that the term "dispersion medium" is not intended to imply a particular amount of the material be present. For example, particularly in a system that utilizes two or more dispersion media (e.g., with different hydrophobic/hydrophilic character), the relative amounts of different dispersion media may be adjusted as desired. For example, the percent of dispersion medium in the composition from which AE nanoparticles are prepared (e.g., in the premix) can range from 0% to 99%, from 10% to 99%, from 25% to 99%, from 50% to 99%, or from 75% to 99%. In some embodiments, the percent of dispersion medium in the composition from which AE nanoparticles are prepared (e.g., in the premix) can range from 0% to 75%, from 0% to 50%, from 0% to 25%, or from 0% to 10%.

In some embodiments, the percent of oil in the composition from which AE nanoparticles are prepared (e.g., in the premix) ranges between 0% to 30%. In some embodiments the percent of oil in the composition from which AE nanoparticles are prepared (e.g., in the premix) is approximately 1%, approximately 2%, approximately 3%, approximately 4%, approximately 5%, approximately 6%, approximately 7%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, approximately 26%, approximately 27%, approximately 28%, approximately 29%, or approximately 30%. In some embodiments the percent of oil is approximately 8%. In some embodiments the percent of oil is approximately 5%.

In some embodiments, the premix comprises oil and surfactant at a ratio ranging between 0.5:1 to 10:1. In some embodiments, the ratio of oil to surfactant is approximately 0.5:1, approximately 1:1, approximately 2:1, approximately 3:1, approximately 4:1, approximately 5:1, approximately 6:1, approximately 7:1, approximately 8:1, approximately 9:1, or approximately 10:1. In some embodiments, the ratio of surfactant to oil is approximately 0.5:1, approximately 1:1, approximately 2:1, approximately 3:1, approximately 4:1, approximately 5:1, approximately 6:1, approximately 7:1, approximately 8:1, approximately 9:1, or approximately 10:1. In some embodiments, the premix comprises oil and surfactant at a ratio ranging between 0.5:1 to 2:1. In some embodiments, the ratio of oil to surfactant is approximately 0.5:1, approximately 1:1, or approximately 2:1. In some embodiments, the ratio of surfactant to oil is approximately 0.5:1, approximately 1:1, or approximately 2:1. In certain embodiments, the ratio of oil to surfactant is approximately 1:1.

Those skilled in the art will recognize that the above presents certain exemplary, not comprehensive, lists of possible dispersion media for use in accordance with the present invention. Any appropriate dispersion medium may be used in the production of AE nanoparticles.

Surfactants

In some embodiments, the premix may optionally comprise one or more substances with surfactant activity. In some embodiments, a substance with surfactant activity can promote the production of AE nanoparticles with increased stability, improved uniformity, or increased viscosity. Surfactants can be particularly useful in embodiments that utilize two or more dispersion media. The percent of substances with surfactant activity in the composition from which AE nanoparticles are prepared (e.g., in the premix) can range from 0% to 99%, from 10% to 99%, from 25% to 99%, from 50% to 99%, or from 75% to 99%. In some embodiments, the percent of substances with surfactant activity in the composition from which AE nanoparticles are prepared (e.g., in the premix) can range from 0% to 75%, from 0% to 50%, from 0% to 25%, or from 0% to 10%.

In some embodiments, the percent of substances with surfactant activity in the composition from which AE nanoparticles are prepared (e.g., in the premix) ranges between 0% to 30%. In some embodiments the percent of substances with surfactant activity in the composition from which AE nanoparticles are prepared (e.g., in the premix) is approximately 1%, approximately 2%, approximately 3%, approximately 4%, approximately 5%, approximately 6%, approximately 7%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, approximately 26%, approximately 27%, approximately 28%, approximately 29%, or approximately 30%. In some embodiments the percent of substances with surfactant activity is approximately 8%. In some embodiments the percent of substances with surfactant activity is approximately 5%.

Any substance with surfactant activity known in the art is suitable for use in making the inventive AE nanoparticles. Such surfactants include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span 85) glycocholate; sorbitan monolaurate (Span 20); polysorbate 20 (Tween-20); polysorbate 60 (Tween-60); polysorbate 65 (Tween-65); polysorbate 80 (Tween-80); polysorbate 85 (Tween-85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. The surfactant component may be a mixture of different surfactants. These surfactants may be extracted and purified from a natural source or may be prepared synthetically in a laboratory. In a preferred embodiment, the surfactants are commercially available.

Those skilled in the art will recognize that this is an exemplary, not comprehensive, list of substances with surfactant activity. Any surfactant may be used in the production of AE nanoparticles.

Biologically Active Agents

Inventive AE nanoparticle compositions may be utilized to deliver one or more biologically active agents. Thus, biologically active agents may be delivered in conjunction with inventive AE nanoparticles. In some embodiments, the biologically active agent is included in the premix. In some embodiments, the biologically active agent is added after AE nanoparticle formation.

Any biologically active agents, including, for example, therapeutic, diagnostic, prophylactic, nutritional, cosmetic, and/or dermatological agents, may be delivered according to the present invention. Such biologically active agents may be small molecules, organometallic compounds, nucleic acids, proteins (including multimeric proteins, protein complexes, etc.), peptides, lipids, carbohydrates, herbs, hormones, metals, radioactive elements and compounds, drugs, vaccines, immunological agents, etc., and/or combinations thereof. Such biologically agents may be encapsulated within, adsorbed to the surface of, and/or present within the micellar membrane of inventive AE nanoparticles.

In some embodiments, the percent of biologically active agent in the premix or in nanoparticles ranges from 0.1% to 25%. In some embodiments, the percentage of biologically active agent in the premix or in nanoparticles ranges from 0.1% to 20%, from 0.1% to 15%, from 0.1% to 10%, from 0.1% to 5%, or from 0.1% to 1%. In some embodiments, the percentage of biologically active agent in the premix or in nanoparticles ranges from 1% to 20%, from 5% to 20%, from 10% to 20%, from 15% to 20%, or from 15% to 25%. In some embodiments, the percentage of biologically active agent in the premix or in nanoparticles is less than 0.1%. In some embodiments, the percentage of biologically active agent in the premix or in nanoparticles is greater than 25%. In some embodiments, the percentage of biologically active agent in the premix or in nanoparticles is approximately 0.1%, approximately 1%, approximately 2%, approximately 3%, approximately 4%, approximately 5%, approximately 6%, approximately 7%, approximately 8%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, approximately 25%, or greater.

Relevant biologically active agents can be produced or obtained according to any available method or approach. Biologically active agents may contain, or be modified to contain, one or more moieties intended to facilitate their use or delivery in conjunction with inventive nanoparticles. Such modification should not interfere with the biological activity of the agent. In some embodiments, the modification can optionally be removed in vivo. For example, biologically active agents may be detectably labeled and/or may be provided in a "pro" form that is converted or modified after delivery into an active form.

In some embodiments, the biologically active agent is a small molecule and/or organic compound with pharmaceutical activity. In some embodiments, the biologically active agent is a clinically-used drug. In some embodiments, the drug is an antibiotic, anti-viral agent, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anticholinergic, analgesic, anti-depressant, anti-psychotic, β-adrenergic blocking agent, diuretic, cardiovascular active agent, vasoactive agent, non-steroidal anti-inflammatory agent, etc.

The biologically active agents delivered may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, the biologically active agent is a diagnostic agent. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, the biologically active agent is a prophylactic agent. In some embodiments, prophylactic agents include vaccines. Vaccines may comprise isolated proteins or peptides, inactivated organisms and viruses, dead organisms and virus, genetically altered organisms or viruses, and cell extracts. Prophylactic agents may be combined with interleukins, interferon, cytokines, and adjuvants such as cholera toxin, alum, Freund's adjuvant, etc. Prophylactic agents may include antigens of such bacterial organisms as Streptococccus pnuemoniae, Haemophilus influenzae, Staphylococcus aureus, Streptococcus pyrogens, Corynebacterium diphtherias, Listeria monocytogenes, Bacillus anthracia, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni, and the like. These antigens may be in the form of whole killed organisms, peptides, proteins, glycoproteins, carbohydrates, or combinations thereof.

In some embodiments, the biologically active agent may be a protein. As used herein, the terms "protein" and "peptide" can be used interchangeably. In certain embodiments, peptides range from about 5 to 40, 10 to 35, 15 to 30, or 20 to 25 amino acids in size. Peptides from panels of peptides comprising random sequences and/or sequences which have been varied consistently to provide a maximally diverse panel of peptides may be used.

In some embodiments, the biologically active agent may be an antibody. In some embodiments, antibodies may include, but are not limited to, polyclonal, monoclonal, chimeric (i.e. "humanized"), single chain (recombinant) antibodies. In some embodiments, antibodies may have reduced effector functions and/or bispecific molecules. In some embodiments, antibodies may include Fab fragments and/or fragments produced by a Fab expression library.

In some embodiments, the biologically active agent may be a nucleic acid. In some embodiments, the oligonucleotides comprise DNA, RNA, chimeric mixtures, derivatives, characteristic portions, and/or modified versions thereof. The oligonucleotides of the present invention may be single-stranded and/or double-stranded. The oligonucleotide may be modified at the base moiety, sugar moiety, and/or phosphate backbone, for example, to improve stability of the molecule, hybridization, etc.

In specific embodiments, a nucleic acid comprises an antisense molecule that binds to a translational start site, transcriptional start site, and/or splice junctions. Antisense oligonucleotides will bind to a target mRNA and/or prevent translation. Alternatively or additionally, the antisense oligonucleotide may bind to DNA of a target gene, such as, for example, a regulatory element.

In some embodiments, a nucleic acid comprises a ribozyme designed to catalytically cleave target mRNA transcripts may be used to prevent translation of a target mRNA and/or expression of a target (see, e.g., PCT publication WO 90/11364; and Sarver et al., 1990, Science 247:1222; both of which are incorporated herein by reference).

Alternatively or additionally, endogenous target gene expression may be reduced by targeting deoxyribonucleotide sequences complementary to the regulatory region of the target gene (i.e., the target gene's promoter and/or enhancers) to form triple helical structures that prevent transcription of the target gene in target muscle cells in the body (see generally, Helene, 1991, Anticancer Drug Des. 6:569; Helene et al., 1992, Ann, N.Y. Acad. Sci. 660:27; and Maher, 1992, Bioassays 14:807; all of which are incorporated herein by reference).

In some embodiments, the biologically active agent is a nutraceutical agent. In some embodiments, the nutraceutical agent provides basic nutritional value. In some embodiments, the nutraceutical agent provides health or medical benefits. In some embodiments, the nutraceutical agent is a dietary supplement.

In some embodiments, the nutraceutical agent is a vitamin. In some embodiments, the vitamin is one or more of vitamin A (retinoids), vitamin B1 (thiamine), vitamin B2 (riboflavin), vitamin B3 (niacin), vitamin B5 (pantothenic acid), vitamin B6 (pyroxidone), vitamin B7 (biotin), vitamin B9 (folic acid), vitamin B12 (cyanocobalamin), vitamin C (ascorbic acid), vitamin D, vitamin E, or vitamin K.

In some embodiments, the nutraceutical agent is a mineral. In some embodiments, the mineral is one or more of bismuth, boron, calcium, chlorine, chromium, cobalt, copper, fluorine, iodine, iron, magnesium, manganese, molybdenum, nickel, phosphorus, potassium, rubidium, selenium, silicon, sodium, strontium, sulfur, tellurium, titanium, tungsten, vanadium, or zinc.

In some embodiments, the nutraceutical agent is an essential amino acid. In some embodiments, the amino acid is one or more of arginine, glutamine, histidine, isoleucine, leucine, lysine, methionine, phenylalanine, threonine, tryptophan, or valine.

In some embodiments, nutraceutical agents may include fatty acids and/or omega-3 fatty acids (e.g. DHA or ARA), fruit and vegetable extracts, lutein, phosphatidylserine, lipoid acid, melatonin, glucosamine, chondroitin, aloe vera, guggul, green tea, lycopene, whole foods, food additives, herbs, phytonutrients, antioxidants, flavonoid constituents of fruits, evening primrose oil, flaxseeds, fish and marine animal oils (e.g. cod liver oil), and probiotics. In some embodiments, nutraceutical agents may include bio-engineered foods genetically-engineered to have a desired property (also known as "pharmafoods").

Exemplary nutraceutical agents and dietary supplements are disclosed, for example, in Roberts et al., (Nutriceuticals: The Complete Encyclopedia of Supplements, Herbs, Vitamins, and Healing Foods, American Nutriceutical Association, 2001; incorporated herein by reference). Nutraceutical agents and dietary supplements are also disclosed in Physicians' Desk Reference for Nutritional Supplements, 1st Ed., 2001 and *Physicians' Desk Reference for Herbal Medicines*, 1st Ed., 2001 (incorporated herein by reference).

In some embodiments, AE nanoparticles loaded with nutraceutical agents can be incorporated into food substances. For example, the nutraceutical-loaded AE nanoparticles can be dissolved into liquids, such as beverages.

In some embodiments, the biologically active agent is a cosmetic and/or dermatological agent. In some embodiments, the cosmetic and/or dermatological agent may optionally include excipients such as sequestering agents, softeners, coloring materials (e.g. pigments and dyes), and fragrances. In some embodiments, the cosmetic and/or dermatological agent may be a composition including, but not limited to, skin softener, nutrition lotion, cleansing lotion, cleansing cream, skin milk, emollient lotion, massage cream, emollient cream, make-up base, lipstick, facial pack or facial gel, cleaner formulation (e.g. shampoos, rinses, body cleanser, hair-tonics, and soaps), and dermatological composition (e.g. lotions, ointments, gels, creams, patches and sprays).

In some embodiments, the cosmetic and/or dermatological agent may include vitamins and their derivatives (e.g. vitamin E and its esters, vitamin C and its esters, vitamins B, vitamin A alcohol or retinol and its esters), provitamins (e.g. panthenol, niacinamide or ergocalciferol), antioxidants, phenolic compounds (e.g. benzoyl peroxide), essential oils, humectants, sunscreen agents, moisturizing agents, proteins, ceramides, and pseudoceramides.

In some embodiments, the biologically active agent may be one or more botulinum toxin peptides or protein complexes. In some embodiments, the botulinum toxin may be one or more of botulinum toxin serotypes A, B, $C_1$, $C_2$, D, E, F, or G. In some embodiments, the botulinum toxin may be an isolated and/or purified botulinum toxin. In some embodiments, the botulinum toxin may be a partially-isolated and/or partially-purified botulinum toxin. In some embodiments, the botulinum toxin may be a native botulinum complex. In some embodiments, the botulinum toxin may be associated with non-toxin proteins. In some embodiments, the botulinum toxin may be a recombinantly-made botulinum toxin.

Those skilled in the art will recognize that this is an exemplary, not comprehensive, list of biologically active agents. Any biologically active agent may be encapsulated within or bound to the surface of AE nanoparticles.

In some embodiments, AE nanoparticles comprising a biologically active agent may optionally include one or more release-retarding ingredients to allow for controlled release of the agent. Any release-retarding ingredient known in the art is suitable for use in making the inventive AE nanoparticles. In some embodiments, release-retarding ingredients are hydrophilic and/or hydrophobic polymers. Release-retarding ingredients include, for example celluloses or derivatives thereof, acrylic polymers, ester polymers, vinyl-pyrrolidone-based polymers, gums, other natural polymers, and/or combinations of these.

In some embodiments, the release-retarding ingredient is cellulose or a derivative thereof. In certain embodiments, the cellulose or derivative thereof comprises one or more of hydroxypropyl methylcellulose, methylcellulose, carboxymethylcellulose, sodium carboxymethylcellulose, hydroxypropyl ethylcellulose, hydroxyethylcellulose, and hydroxypropyl cellulose. In certain embodiments, the cellulose or derivative thereof is methylcellulose or a derivative thereof. In certain embodiments, the cellulose or derivative thereof is hydroxypropyl methylcellulose (HPMC). Those skilled in the art will appreciate that other cellulosic polymers, including other alkyl cellulosic polymers, can be utilized.

In some embodiments, the release-retarding ingredient is an acrylic polymer. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers. The acrylic polymer may comprise fully polymerized copolymers of acrylic and methacrylic acid esters with a low content of quaternary ammonium groups.

In some embodiments, the release-retarding ingredient is a polyester. In some embodiments, polyesters include polyalkylene glycols, poly(glycolide-co-lactide), PEGylated poly(lactic-co-glycolic acid), poly(lactic acid), PEGylated poly(lactic acid), poly(glycolic acid), PEGylated poly(glycolic acid), co-polymers of polylactic and polyglycolic acid, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), and derivatives thereof. In some embodiments, polyesters include, for example, polycaprolactone, poly(L-lactide-co-L-lysine), poly(serine ester), poly(4-hydroxy-L-proline ester), poly[$\alpha$-(4-aminobutyl)-L-glycolic acid], and derivatives thereof.

In some embodiments, the release-retarding ingredient is a cross-linked polymer of poly(vinyl-pyrrolidone). In some embodiments, the polymer is crosspovidone. In some embodiments, the polymer is un-cross-linked poly(vinyl-pyrrolidone). In some embodiments, the polymer is povidone.

In some embodiments, the release-retarding ingredient may be a natural polymer. In some embodiments, the natural polymer is a gum, including, for example, xanthan gum, alginic acid, caraya gum, sodium alginate, and/or locust bean gum. In some embodiments, the natural polymer may be a protein (e.g. albumin), lipid, nucleic acid, or carbohydrate.

Methods of Making AE Nanoparticles

In general, inventive nanoparticle compositions (e.g., botulinum nanoparticle compositions) may be prepared by any available method. In some embodiments, nanoparticle compositions are prepared by chemical means. However, chemical means often require toxic (typically organic) solvents; in some embodiments, nanoparticle compositions are prepared in accordance with the present invention without utilizing such solvents.

In certain embodiments of the present invention, nanoparticle compositions are prepared by preparing a premix and subjecting the premix to high shear forces. As used herein, the term "shear force" refers to a force that is parallel to the face of a material, as opposed to a force that is perpendicular to the face of a material.

Any method known in the art can be used to generate high shear forces. According to the present invention, the use of mechanical energy (i.e., high shear forces) can replace or minimize any requirement to use costly and/or toxic chemical solvents; can increase the speed at which nanoparticles assemble, can increase the yield of nanoparticles generated in a particular mix of components, and/or can greatly reduce the overall cost of preparing nanoparticle compositions. Furthermore, in those embodiments in which an agent such as a biologically active agent (e.g., botulinum toxin) is incorporated into inventive nanoparticle compositions, the use of high shear force can increase the loading capacity of the nanoparticle as compared to traditional methods of forming nanoparticles. In traditional methods, loading of agents within or on the surface of nanoparticles typically relies on diffusion of the agent to the interior and/or to the surface of the nanoparticle. According to the present invention, the use of high shear force can allow for the manufacture of smaller particles (e.g., on average) and/or a more narrow distribution of particle sizes in a nanoparticle composition.

In some embodiments, high shear forces are achieved by exposure to high pressure, for example by continuous turbulent flow at high pressure, for example about 15,000 psi. In some embodiments, such high pressure is within the range of about 18,000 to about 26,000 psi; in some embodiments, it is within the range of about 20,000 to 25,000 psi. In some embodiments, high shear forces are characterized by pressures of at least 3,000 psi, 10,000 psi, 15,000 psi, 18,000 psi, 20,000 psi, 22,000 psi, or 24,000 psi. In some embodiments, high shear forces are characterized by pressures of 16,000 psi, 17,000 psi, 18,000 psi, 19,000 psi, 20,000 psi, 21,000 psi, 22,000 psi, 23,000 psi, 24,000 psi, or 25,000 psi.

In some embodiments, cavitation is used to generate high shear forces. In some embodiments, high pressure homogenization is used to generate high shear forces.

In some embodiments, high shear force may be administered by passage through an instrument such as, for example, a Microfluidizer® Processor (Microfluidics Corporation/MFIC Corporation) or other like device. Microfluidizer® Processors provide high pressure and a resultant high shear rate by accelerating the product through microchannels to a high velocity for size reduction to the nanoscale range. The fluid is split in two and is pushed through microchannels with typical dimensions in the order of 75 microns at high velocities (in the range of 50-300 m/s). As the fluid exits the microchannels it forms jets which collide with jets from opposing microchannels. In the channels the fluid experiences high shear (up to $10^7$ 1/s) which is orders of magnitude higher than that of conventional technologies. Jet collisions result in mixing in submicron level. Therefore, high shear and impact are responsible for particle size reduction and mixing of multiphase fluids in the Microfluidizer® technology.

In some embodiments of the present invention, a sample is "microfluidized" through exposure to high shear forces for a period of time less than about 10 minutes. In some embodiments, the period of time is less than about 9, 8, 7, 6, 5, 4, 3, 2, or 1 minute(s). In some embodiments, the period of time is within the range of about 1-2 minutes or less; in some embodiments, the period of time is about 30 seconds.

In some embodiments of the invention, a sample is "microfluidized" through a single exposure to high shear forces; such embodiments are referred to herein as "single pass" microfluidization.

The present invention encompasses the recognition that subjecting a premix to high shear forces can generate a nanoparticle composition, and in particular can generate a uniform nanoparticle composition.

In some embodiments of the present invention, all of the components present in the final nanoparticle composition are present in the premix and are subjected to high shear force to produce the nanoparticle composition. In some embodiments of the present invention, one or more of the components that are present in the final nanoparticle composition is/are missing from the premix or is/are present in the premix in a smaller amount than in the final nanoparticle composition. That is, in some embodiments of the present invention, one or more materials are added to the nanoparticle composition after the premix is subjected to high shear force.

In certain embodiments of the invention, the premix is prepared as a solution prior to application of high shear force. In particular, for nanoparticle compositions that include at least one biologically active agent (e.g., botulinum toxin), it is often desirable for the biologically active agent to be dissolved in the premix before the high shear force is applied. Thus, in many embodiments, the biologically active agent is soluble in at least one of the media (or in a combination of media utilized in the premix). In some embodiments of the invention, such dissolution requires heating; in other embodiments it does not.

In some embodiments of the present invention, the premix components may assemble into particles before the application of high shear force. At least some of such particles may be microparticles or even nanoparticles. In some embodiments, an inventive nanoparticle composition is prepared from a premix, wherein the premix is selected from the group comprising a suspension or a microemulsion. In some embodiments, however, particle structures do not form in the premix before application of high shear force.

Methods of Use

In some embodiments, the present invention provides methods of using AE nanoparticles and/or nanoparticle compositions by delivering them (optionally in conjunction with a biologically active agent or other substance) to a subject. Such delivery may be via any route. For example, delivery may be orally, parenterally, intracisternally, intravaginally, subcutaneously, intraperitoneally, intramuscularly, intravenously, transdermally (topically), intradermally, bucally, rectally, and/or opthalmically.

In some embodiments, the invention provides methods of transdermally delivering a biologically active agent to a subject by administering to the subject one or more AE nanoparticles to the surface of the subject's skin, wherein the biologically active agent is contained within or bound to the surface of the AE nanoparticles. In some embodiments, the subject may be a mammal (e.g. human)

In some embodiments, a composition for transdermal delivery of a biologically active agent may comprise AE nanoparticles containing the agent to be delivered. In some embodiments, the biologically active agent may be encapsulated within the AE nanoparticles. In some embodiments, the biologically active agent may be bound to the surface of the AE nanoparticles.

Traditionally, attempts at transdermal administration of substances have required a step of improving the permeability of the skin before the substance is applied. Some attempts have included using chemical penetration enhancing agents that act on the skin's surface to increase the permeability of substances through the skin. The use of these chemical penetration enhancing agents is often painful and may damage the surface of the skin. Other attempts have included the use of ultrasound or iontophoresis or other forms of energy to facilitate the permeation of substances through the skin as well as micro-puncture or high-energy techniques to create micro-channels across the surface layers of the skin, such as the stratum corneum. The AE nanoparticles of the present invention can achieve transdermal delivery of a biologically active agent without requiring the use of abrasive or other skin-disrupting agents (whether chemical, mechanical, electrical, magnetic, etc.).

In some embodiments, a composition for transdermal delivery of a composition comprising AE nanoparticles for transdermal delivery of a biologically active agent may be in the form of a cosmetic formulation including, but not limited to, a skin softener, nutrition lotion type emulsion, cleansing lotion, cleansing cream, skin milk, emollient lotion, massage cream, emollient cream, make-up base, lipstick, facial pack or facial gel, cleaner formulation (e.g. shampoos, rinses, body cleanser, hair-tonics, or soaps), and dermatological composition (e.g. lotions, ointments, gels, creams, patches or sprays).

In some embodiments, a composition for transdermal delivery of a biologically active agent may be in the form of a transdermal patch. The use of adhesive patches is well known in the art (for example, see U.S. Pat. No. 296,006 (design); U.S. Pat. Nos. 6,010,715; 5,591,767; 5,008,110; 5,683,712; 5,948,433; and 5,965,154. In some embodiments, the transdermal patch may comprise an adhesive layer, which may be applied to a person's skin. In some embodiments, the transdermal patch may comprise a depot or reservoir for holding a biologically active agent or composition. In some embodiments, the transdermal patch comprises an exterior surface that may prevent leakage of the agent or composition from the depot. In some embodiments, the exterior surface of a patch may be non-adhesive.

In some embodiments, the composition comprising AE nanoparticles for transdermal delivery of a biologically active agent may be incorporated into a patch so that the AE nanoparticles remain stable for extended periods of time. The AE nanoparticles may be incorporated into a polymeric matrix that stabilizes the AE nanoparticles and permits the AE nanoparticles to diffuse from the matrix and from the patch. In some embodiments, the AE nanoparticles may be incorporated into the adhesive layer of the patch. In one embodiment, the adhesive layer may be heat-activated. In certain embodiments, temperatures of about 37° C. may cause the adhesive to slowly liquefy so that the AE nanoparticles diffuse through the skin. In certain embodiments, the adhesive may remain tacky when stored at less than 37° C. In some embodiments, the adhesive loses its tackiness as it liquefies at temperatures of about 37° C. In some embodiments, the administration of the AE nanoparticles is complete once the patch no longer adheres to the skin.

In some embodiments, the compositions comprising AE nanoparticles for transdermal delivery of a biologically active agent may be used in an application device that permits application of the composition to a target site on the skin without applying the composition to non-target site areas of the skin. In some embodiments, a device may be employed that allows the composition to be applied without first applying the composition to one's fingers, which may lead to undesirable paralysis of the fingers. Suitable devices include spatulas, swabs, syringes without needles, and adhesive patches. Use of spatulas or swabs, or the like may require the device to be inserted into a container containing the composition. Using syringes or adhesive patches may be accomplished by filling the syringe or patch with the composition. The composition may be topically spread by the spatulas or swabs, or may be expelled from the syringes onto the person's skin.

In some embodiments, the biologically active agent may be one or more botulinum toxin peptides or protein complexes. In some embodiments, the botulinum toxin may be one or more of botulinum toxin serotypes A, B, $C_1$, $C_2$, D, E, F, or G. In some embodiments, the botulinum toxin may be an isolated and/or purified botulinum toxin. In some embodiments, the botulinum toxin may be a partially-isolated and/or partially-purified botulinum toxin. In some embodiments, the botulinum toxin may be a native botulinum complex. In some embodiments, the botulinum toxin may be associated with non-toxin proteins. In some embodiments, the botulinum toxin may be a recombinantly-made botulinum toxin.

In some embodiments, the botulinum toxin within a composition for transdermal delivery may be present in an amount so that between about $10^{-3}$ U/kg and 10 U/kg pass through a patient's skin. In some embodiments, the botulinum toxin may be present in an amount so that between about $10^{-2}$ U/kg and about 1 U/kg pass through the patient's skin. In some embodiments, the botulinum toxin may be present in an amount so that between about $10^{-1}$ U/kg and about 1 U/kg pass through the patient's skin. In some embodiments, the botulinum toxin may be present in an amount so that between about 0.1 U and about 5 U pass through the patient's skin. As used herein, "Units" ("U") are biologically equivalent or bioactively equivalent to Units defined by commercial manufacturers of botulinum toxin.

In one embodiment, dosages of botulinum toxin can range from as low as about 1 U to as high as about 20,000 U. The particular dosages may vary depending on the condition being treated and therapeutic regime being utilized. For example, treatment of subdermal, hyperactive muscles may require high transdermal dosages (for example, 200 U to 20,000 U) of botulinum toxin. In comparison, treatment of neurogenic inflammation or hyperactive sweat glands may require relatively small transdermal dosages (for example, about 1 U to about 1,000 U) of botulinum toxin. In some embodiments, the composition may comprise an amount of botulinum toxin sufficient to achieve a therapeutic effect lasting between 1 month and 5 years. In some embodiments, the composition comprising botulinum toxin may be formulated to avoid potential complications including, but not limited to, systemic toxicity or botulism poisoning.

In some embodiments, the present invention provides methods of treating facial wrinkles. In some embodiments, nanoparticle compositions comprising AE nanoparticles for the transdermal delivery of a biologically active agent may be used to treat facial wrinkles. In some embodiments, nanoparticle compositions comprising AE nanoparticles for the transdermal delivery of botulinum toxin may be used to treat facial wrinkles. In some embodiments, facial wrinkles may include glabellar wrinkles, facial lines (e.g. hyperkinetic facial lines), forehead frown lines, midfacial wrinkles, mouth wrinkles, neck lines and banding (e.g. platysma bands), and chin creases.

In some embodiments, the present invention provides methods of treating neuromuscular disorders and conditions in a subject. In some embodiments, nanoparticle compositions comprising AE nanoparticles for the transdermal delivery of a biologically active agent may be used to treat neuromuscular disorders and conditions involving muscular spasm and/or contracture. In some embodiments, nanoparticle compositions comprising AE nanoparticles for the transdermal delivery of botulinum toxin may be used to treat neuromuscular disorders and conditions. In some embodiments, neuromuscular disorders and conditions involving muscular spasm and/or contracture include, but are not limited to, various forms of palsy, facial contracture, dystonia, hemifacial spasm, tremor, spasticity (e.g. resulting from multiple sclerosis), retroorbital muscle, and various other ophthalmologic conditions (Carruthers et al., 1996, *J. Am. Acad. Dermatol.*, 34:788; incorporated herein by reference). In some embodiments, the present invention does not provide methods of treating neuromuscular disorders and conditions involving muscular spasm and/or contracture in a subject.

In some embodiments, the present invention provides methods of treating hyperhidrosis (i.e., a medical condition in which a person sweats excessively and unpredictably) in a subject. In some embodiments, nanoparticle compositions comprising AE nanoparticles for the transdermal delivery of a biologically active agent may be used to treat hyperhidrosis. In some embodiments, nanoparticle compositions comprising AE nanoparticles for the transdermal delivery of botulinum toxin may be used to treat hyperhidrosis. In some embodiments, the present invention does not provide methods of treating hyperhidrosis in a subject.

In some embodiments, the present invention provides methods of treating headache in a subject. In some embodiments, nanoparticle compositions comprising AE nanoparticles for the transdermal delivery of a biologically active agent may be used to treat headache. In some embodiments, nanoparticle compositions comprising AE nanoparticles for the transdermal delivery of botulinum toxin may be used to treat headache. In some embodiments, the present invention does not provide methods of treating headache in a subject.

In some embodiments, the present invention provides methods of treating prostate hyperplasia in a subject. In some embodiments, nanoparticle compositions comprising AE nanoparticles for the transdermal delivery of a biologically active agent may be used to treat prostate hyperplasia. In some embodiments, nanoparticle compositions comprising AE nanoparticles for the transdermal delivery of botulinum toxin may be used to treat prostate hyperplasia. In some embodiments, the present invention does not provide methods of treating prostate hyperplasia in a subject.

In some embodiments, the present invention provides a method of imaging a disorder (e.g. cancer) in a subject by labeling one or more AE nanoparticles with a reporter group and with a targeting agent that binds to a target associated with the disorder; administering the labeled particles to the subject under conditions and in an amount sufficient to bind to the target; and imaging the reporter group, thereby imaging the disorder.

In some embodiments, the inventive AE nanoparticles are used to deliver drugs to a subject. In some embodiments, nanoparticle compositions may comprise AE nanoparticles which contain drugs, including but not limited to, antibiotics, anti-viral agents, anesthetics, anticoagulants, anti-cancer agents, inhibitors of enzymes, steroidal agents, anti-inflammatory agents, anti-neoplastic agents, antigens, vaccines, antibodies, decongestants, antihypertensives, sedatives, birth control agents, progestational agents, anti-cholinergics, analgesics, anti-depressants, anti-psychotics, β-adrenergic blocking agents, diuretics, cardiovascular active agents, vasoactive agents, hormones (e.g. insulin, estradiol), and non-steroidal anti-inflammatory agents.

Pharmaceutical Compositions

The present invention provides AE nanoparticles. In some embodiments, the present invention provides for pharmaceutical compositions comprising AE nanoparticles, as described herein. The present invention provides pharmaceutical compositions comprising AE nanoparticles containing a therapeutically effective amount of a biologically active agent. Such pharmaceutical compositions may optionally comprise one or more additional therapeutically-active substances. In accordance with one embodiment, a method of administering a pharmaceutical composition comprising AE nanoparticles containing a therapeutically effective amount of a therapeutic agent to a patient in need thereof. In some embodiments, the compositions are administered to humans.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail (1977, *J. Pharm. Sci.,* 66:1; incorporated herein by reference). Salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. In certain embodiments, the esters are cleaved by enzymes such as esterases.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series and in E. B. Roche, ed., *Bioreversible Carriers in Drug Design*, American Pharmaceutical Association and Pergamon Press, 1987 (both of which are incorporated herein by reference).

As described above, the pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006) discloses various carriers used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can also be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytouened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

The pharmaceutical compositions may be administered to animals, preferably mammals (e.g., domesticated animals, cats, dogs, mice, rats), and more preferably humans Any method of administration may be used to deliver the pharmaceutical compositions to the animal. In certain embodiments, the pharmaceutical composition is administered orally. In other embodiments, the pharmaceutical composition is administered parenterally.

In some embodiments of the invention, a method for the treatment of facial wrinkles is provided comprising administering a therapeutically effective amount of AE nanoparticles comprising botulinum toxin to a subject in need thereof, in such amounts and for such time as is necessary to achieve the desired result. In certain embodiments of the present invention a "therapeutically effective amount" of the AE nanoparticles comprising botulinum toxin is that amount effective for treating facial wrinkles including, but not limited to, glabellar wrinkles, facial lines (e.g. hyperkinetic facial lines), forehead frown lines, midfacial wrinkles, mouth wrinkles, neck lines and banding (e.g. platysma bands), and chin creases.

In some embodiments of the invention, a method for the treatment of hyperhidrosis is provided comprising administering a therapeutically effective amount of AE nanoparticles comprising botulinum toxin to the hands, feet, and/or underarms of a subject in need thereof, in such amounts and for such time as is necessary to achieve the desired result.

The compositions, according to the method of the present invention, may be administered using any amount and any route of administration effective for treating facial wrinkles. The exact amount required will vary from subject to subject, depending on the species, age, and general condition of the subject, the severity of the infection, the particular composition, its mode of administration, its mode of activity, and the like. The compositions of the invention are preferably formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The pharmaceutical compositions of the present invention may be administered by any route. In some embodiments, the pharmaceutical compositions of the present invention are administered variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, bucal, enteral, sublingual, and/or as an oral spray, nasal spray, and/or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such an Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active component is admixed under sterile conditions with a pharmaceutically acceptable carrier and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, the rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662 (all of which are incorporated herein by reference). Intradermal compositions may be administered by devices which limit the effective penetration length of a needle into the skin, such as those described in PCT publication WO 99/34850 (incorporated herein by reference) and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537; all of which are incorporated herein by reference. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65.degree. F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 nm to about 200 nm.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 nm to about 200 nm, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1%/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

It will also be appreciated that the compounds and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

The pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive compound may be administered concurrently with another agent used to treat the same disorder), and/or they may achieve different effects (e.g., control of any adverse effects).

The pharmaceutical compositions of the present invention may be administered alone and/or in combination with other agents that are used to treat the symptoms of facial wrinkles. To give but a few examples, the pharmaceutical compositions of the present invention could be administered in combination with agents such as retinoic acid, vitamin C and/or E, and/or hyaluronic acid, pentapeptides (e.g., lys-thr-thr-lys-ser), and/or hexapeptides (e.g., acetyl hexapeptide-3, also known as Argircline), depending on the route of administration. Novel compositions comprising pentapeptides and hexapeptides are further described in PCT application serial number PCT/US07/086040 entitled "Peptide Nanoparticles and Uses Therefor," filed on Nov. 30, 2007.

In will further be appreciated that therapeutically active agents utilized in combination may be administered together in a single composition or administered separately in different compositions.

In general, it is expected that agents utilized in combination with be utilized at levels that do not exceed the levels at which they are utilized individually. In some embodiments, the levels utilized in combination will be lower than those utilized individually.

General considerations in the formulation and/or manufacture of pharmaceutical agents may be found, for example, in *Remington: The Science and Practice of Pharmacy* 21$^{st}$ ed., Lippincott Williams & Wilkins, 2005.

Kits

In some embodiments, the present invention relates to a kit for conveniently and/or effectively carrying out the methods in accordance with the present invention. In general, an inventive pharmaceutical pack and/or kit comprises one or more containers filled with one or more of the ingredients of the pharmaceutical compositions of the invention. Such kits are especially suited for the delivery of solid oral forms such as tablets and/or capsules. In some embodiments, such a kit includes a number of unit dosages, and may include a card having the dosages oriented in the order of their intended use. A memory aid may be provided, for example in the form of numbers, letters, and/or other markings and/or with a calendar insert, designating the days in the treatment schedule in which the dosages can be administered. Alternatively, placebo dosages, and/or calcium dietary supplements, either in a form similar to or distinct from the dosages of the pharmaceutical compositions, may be included to provide a kit in which a dosage is taken every day. Optionally associated with such container(s) may be a notice in the form prescribed by a governmental agency regulating the manufacture, use and/or sale of pharmaceutical products, which notice reflects approval by the agency of manufacture, use and/or sale for human administration.

The invention provides a kit comprising AE nanoparticles of the invention and/or instructional materials which describe administering the inventive AE nanoparticles to a cell and/or a tissue of a subject. In another embodiment, a kit may comprise a dispersion medium suitable for dissolving and/or suspending the inventive AE nanoparticles prior to administering the compound to the subject.

EXEMPLIFICATION

The following examples are only intended to provide illustrations of specific embodiments contemplated by the present invention. The examples are not intended in any way to be limiting.

Example 1: Formulation of a Self-Assembling Pullulan and Polycaprolactone Nanosphere A mixture of 2.5 g of soybean oil and 2.5 g polysorbate 80 (Tween-80) was prepared. The mixture was stirred and heated at 40° C. for 5 minutes. 50 ml deionized water was added, and the resulting mixture was stirred and heated at 40° C. for 10 minutes. 5 ml DMSO containing 0.905 g pullulan and polycaprolactone was added, and the resulting mixture was stirred and heated at 45° C. for 10 minutes. 5 ml was taken for a pre-process sample. The remaining mixture was microfluidized in a single pass at 24,000 psi. The particle size of the pre-process sample was >4000 nm. The particle size after microfluidization was 155 nm.

Example 2: Sample Preparation for Microfluidized Sample (Per Sample)

A mixture of 100 µl of microfluidized sample and 900 µl of reagent (0.1 M sodium phosphate buffer, 1 mM EDTA, 0.25% Triton X-100, 160 IU/mL of triglyceride hydrolase, and 1 IU/ml of cholesterol esterase) was prepared in a 8 ml glass vial.

The resulting mixture was incubated at ambient temperature in the dark for 1 hour. 100 µl of 5% sodium dodecyl sulfate was added, and the resulting mixture was vortexed for 30 seconds. 1 ml of ethanol was added, and the resulting mixture was vortexed for 30 seconds. 100 µl of an internal standard was added, and the resulting mixture was vortexed for 30 seconds. 4 ml of a 1:1 mixture of hexane:ether with 1% ethanol and 0.1% BHT was added. Ethanol and BHT stabilize the ether to prevent peroxide formation. The resulting mixture was vortexed for 60 seconds then centrifuged for 2 minutes on medium speed. The supernatant was extracted with a glass pipet and was stored at −80° C. for up to 30 days. The supernatant was evaporated and redissolved in 40 µl of methanol. 30 µl was injected into an high-pressure liquid chromatography (HPLC) apparatus.

Example 3: Botulinum Toxin a Formulation with Pullulan and Polycaprolactone

A mixture of 1.6 g of soybean oil and 1.6 g of polysorbate 80 (Tween-80) is prepared and stirred for five minutes. In a separate container, a mixture of 100 ng of botulinum toxin A and 20 ml 0.9% saline is prepared and stirred for five minutes. The mixture of saline and botulinum toxin A is added to the mixture of oil and Tween-80 and stirred for 10 minutes. 5 ml of DMSO containing 0.905 grams pullulan and polycaprolactone are added, and the resulting mixture is stirred for 10 minutes. A 5 ml pre-process sample is taken. The remaining mixture is microfluidized in a single pass at 24,000 psi. The particle size before and after microfluidization is measured.

Example 4: Vitamin E Formulation with Pullulan and Polycaprolactone

A mixture of 2.5 g soybean oil and 1 g vitamin E is prepared. 2.5 g polysorbate 80 (Tween-80) is added. The resulting mixture is stirred and heated at 40° C. for 5 minutes. 50 ml water is added to the mixture, and the resulting mixture is stirred and heated at 40° C. for 10 minutes. 5 ml DMSO containing 0.905 g pullulan and polycaprolactone is added. The resulting mixture is stirred and heated at 45° C. for 10 minutes. A 5 ml pre-process sample is taken. The remaining mixture is microfluidized in a single pass at 24,000 psi. The particle size before and after microfluidization is measured.

Example 5: Tocopherol (Vitamin E) Analysis

Delta tocopherol concentrations can be measured for a patient blood plasma or for nanoparticle compositions. Delta tocopherol concentrations are determined by adding 200 µL of plasma or nanoparticle composition with 10 µL of retinyl acetate (internal standard; 10 µg/mL) and 200 µL of ethanol containing butylated hydroxytoluene (BHT) (10 mg/L) and 1.0 mL hexane followed by vortex mixing. The samples are centrifuged at 500× g for 5 minutes and the organic layer transferred to fresh tube. The sample residues are re-extracted with 1.0 mL of hexane and the organic layers are combined. The organic layers are evaporated under $N_2$ and reconstituted with 200 µL of ethanol containing BHT (10 mg/dL) and injected into an HPLC. The HPLC system is a Model 5600 CoulArray 8-channel system with two Model 580 pumps, a high-pressure gradient mixer, a peek pulse damper, a Model 540 autoinjector, a CoulArray Thermostatic Chamber and a serial array of eight coulometric electrodes (ESA Laboratories, Inc., Chelmsford, Mass., USA). The column is a 3.0×150 mm, 3 µM, Supelcosil LC-18 (Supelco, Bellefonte, Pa., USA). The mobile phase consists of methanol/1Propanol/1 M ammonium acetate (78:20:2 v:v:v) at a flow rate of 0.8 mL/min. The concentrations of delta tocopherol are determined by external standardization using purified solutions of delta tocopherol standards (Sigma Chemicals, St. Louis, Mo., USA).

EQUIVALENTS AND SCOPE

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. For example, it is to be understood that any of the compositions of the invention can be used for inhibiting the formation, progression, and/or recurrence of adhesions at any of the locations, and/or due to any of the causes discussed herein or known in the art. It is also to be understood that any of the compositions made according to the methods for preparing compositions disclosed herein can be used for inhibiting the formation, progression, and/or recurrence of adhesions at any of the locations, and/or due to any of the causes discussed herein or known in the art. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention (e.g., any amphiphilic entity, any component of an amphiphilic entity, any polymer, any biologically active agent, any surfactant, any dispersion medium, any release-retarding ingredient, any AE nanoparticle or composition comprising any AE nanoparticle, any route or location of administration, any purpose for which a composition is administered, etc.), can be excluded from any one or more claims. For purposes of brevity, all of the embodiments in which one or more elements, features, purposes, or aspects are excluded are not set forth explicitly herein.

I claim:

1. A method for treating a subject having a dermatological condition, the method comprising transdermally administering to the subject a nanoemulsion comprising a population of particles in a dispersion medium and a botulinum toxin,
    wherein the nanoemulsion comprises oily particles dispersed within an aqueous dispersion medium, or wherein the nanoemulsion comprises aqueous particles dispersed within an oily dispersion medium;
    wherein the majority of particles have diameters between 10 and 300 nanometers;
    wherein the particles comprise one or more amphiphilic entities;
    wherein said one or more amphiphilic entities is hyaluronic acid,
    wherein the nanoemulsion penetrates the skin of the subject without changing or altering the structure of the skin; thereby treating the subject having the dermatological condition.

2. The method of claim 1, wherein the one or more amphiphilic entities comprise a pullulan component and a polycaprolactone component.

3. The method of claim 1, wherein fewer than 5% of the particles have a diameter in excess of 300 nm.

4. The method of claim 1, wherein the difference between the minimum particle diameter and the maximum particle diameter does not exceed approximately 600 nm.

5. The method of claim 1, wherein the difference between the minimum particle diameter and the maximum particle diameter does not exceed approximately 300 nm.

6. The method of claim 1, wherein the difference between the minimum particle diameter and the maximum particle diameter does not exceed approximately 100 nm.

7. The method of claim 1, wherein the majority of particles have diameters below a specified size and within a specified range.

8. The method of claim 1, wherein more than 70% of the majority of particles have diameters below a specified size and within a specified range.

9. The method of claim 1, wherein more than 90% of the majority of particles have diameters below a specified size and within a specified range.

10. The method of claim 1, wherein more than 99.5% of the majority of particles have diameters below a specified size and within a specified range.

11. The method of claim 1, wherein more than 99.9% of the majority of particles have diameters below a specified size and within a specified range.

12. The method of claim 1, wherein the particles have an average diameter ranging between 50-250 nm.

13. The method of claim 1, wherein the nanoemulsion comprises an oil and a surfactant.

14. The method of claim 13, wherein the oil and surfactant are present in a ratio ranging from 0.5-2.0.

15. The method of claim 14, wherein the percent of oil in the nanoemulsion ranges from 1%-30%.

16. The method of claim 1, wherein the botulinum toxin (a) is encapsulated within the particles; (b) is nestled within the particle membrane; (c) is associated with the particle surface; or a combination thereof.

17. The method of claim 1, wherein the nanoparticle composition nanoemulsion has a zeta potential ranging between −25 mV to +25 mV.

18. The method of claim 1, wherein the nanoemulsion penetrates the top layer of the skin of the subject without the use of skin permeation enhancers or abrasives.

19. The method of claim 1, wherein the nanoemulsion was generated by microfluidization.

20. The method of claim 19, wherein the microfluidization is a single-pass microfluidization.

* * * * *